US009849276B2

(12) United States Patent
Ziebol et al.

(10) Patent No.: US 9,849,276 B2
(45) Date of Patent: Dec. 26, 2017

(54) METHOD OF DELIVERING ANTIMICROBIAL TO A CATHETER

(75) Inventors: Robert J. Ziebol, Blaine, MN (US); Keith J. Modert, Vadnais Heights, MN (US)

(73) Assignee: Pursuit Vascular, Inc., Maple Grove, MN (US)

( * ) Notice: Subject to any disclaimer, the term of this patent is extended or adjusted under 35 U.S.C. 154(b) by 1177 days.

(21) Appl. No.: 13/547,572

(22) Filed: Jul. 12, 2012

(65) Prior Publication Data
US 2013/0184679 A1 Jul. 18, 2013

Related U.S. Application Data

(60) Provisional application No. 61/506,979, filed on Jul. 12, 2011.

(51) Int. Cl.
*A61M 39/16* (2006.01)
*A61M 25/00* (2006.01)
*A61M 39/20* (2006.01)

(52) U.S. Cl.
CPC .......... *A61M 39/16* (2013.01); *A61M 25/00* (2013.01); *A61M 39/162* (2013.01); *A61M 39/20* (2013.01); *A61M 25/0017* (2013.01); *A61M 2025/0019* (2013.01); *A61M 2025/0056* (2013.01)

(58) Field of Classification Search
CPC ...... A61M 25/0017; A61M 2025/0018; A61M 2025/0019; A61M 2025/0056; A61M 39/162; A61M 39/20; A61L 29/08; A61L 2420/02; A61L 2300/404; A61L 2300/606
See application file for complete search history.

(56) References Cited

U.S. PATENT DOCUMENTS

| 3,262,448 A | 7/1966 | Ring et al. |
| 3,595,241 A | 7/1971 | Sheridan |
| 4,331,783 A | 5/1982 | Stoy |
| 4,337,327 A | 6/1982 | Stoy |
| 4,369,294 A | 1/1983 | Stoy |
| 4,370,451 A | 1/1983 | Stoy |
| 4,379,874 A | 4/1983 | Stoy |

(Continued)

FOREIGN PATENT DOCUMENTS

| CN | 102202716 | 9/2011 |
| DE | 3515665 | 5/1986 |

(Continued)

OTHER PUBLICATIONS

File History from related U.S. Appl. No. 12/605,963, downloaded Jun. 3, 2015, 191pages.

(Continued)

*Primary Examiner* — Bhisma Mehta
*Assistant Examiner* — Larry R Wilson
(74) *Attorney, Agent, or Firm* — Pauly, DeVries Smith & Deffner LLC

(57) ABSTRACT

A system, method, and article for delivering an antimicrobial agent into the lumen of a trans-dermal catheter are disclosed. In an embodiment, the system comprises an elongate member configured for insertion into a lumen of a catheter, and the elongate member containing an antimicrobial. In the alternative an antimicrobial agent can be placed on an interior surface of a retaining ring.

28 Claims, 14 Drawing Sheets

(56) References Cited

U.S. PATENT DOCUMENTS

| | | |
|---|---|---|
| 4,420,589 A | 12/1983 | Stoy |
| 4,446,967 A | 5/1984 | Halkyard |
| 4,559,043 A | 12/1985 | Whitehouse et al. |
| 4,624,664 A | 11/1986 | Peluso et al. |
| 4,631,188 A | 12/1986 | Stoy |
| 4,705,790 A | 11/1987 | Hubele et al. |
| 4,769,013 A | 9/1988 | Lorenz et al. |
| 4,808,158 A | 2/1989 | Kreuzer et al. |
| 4,894,056 A | 1/1990 | Bommarito |
| 5,015,238 A | 5/1991 | Solomon et al. |
| 5,071,413 A | 12/1991 | Utterberg et al. |
| 5,154,920 A | 10/1992 | Flesher et al. |
| 5,240,675 A | 8/1993 | Wilk et al. |
| 5,297,310 A | 3/1994 | Cox et al. |
| 5,337,730 A | 8/1994 | Maguire |
| 5,366,505 A | 11/1994 | Farber |
| 5,370,640 A | 12/1994 | Kolff |
| 5,375,589 A | 12/1994 | Bhatta |
| 5,407,807 A | 4/1995 | Markus |
| 5,409,012 A | 4/1995 | Sahatjian |
| 5,628,733 A | 5/1997 | Zinreich et al. |
| 5,782,808 A * | 7/1998 | Folden .............. A61M 39/16 604/265 |
| 5,902,631 A | 5/1999 | Wang et al. |
| 5,951,519 A | 9/1999 | Utterberg |
| 6,045,623 A | 4/2000 | Cannon |
| 6,059,107 A | 5/2000 | Nøsted et al. |
| 6,071,413 A | 6/2000 | Dyke et al. |
| 6,183,450 B1 | 2/2001 | Lois |
| 6,232,406 B1 | 5/2001 | Stoy |
| 6,409,716 B1 | 6/2002 | Sahatjian et al. |
| 6,444,318 B1 | 9/2002 | Guire et al. |
| 6,605,294 B2 | 8/2003 | Sawhney |
| 6,605,751 B1 | 8/2003 | Gibbins et al. |
| 6,634,498 B2 | 10/2003 | Kayerød et al. |
| 6,725,492 B2 | 4/2004 | Moore et al. |
| 7,097,850 B2 | 8/2006 | Chappa et al. |
| 7,195,615 B2 | 3/2007 | Tan |
| 7,442,402 B2 | 10/2008 | Chudzik et al. |
| 7,922,701 B2 | 4/2011 | Buchman et al. |
| 8,500,717 B2 | 8/2013 | Becker |
| 8,622,995 B2 | 1/2014 | Ziebol et al. |
| 8,622,996 B2 | 1/2014 | Ziebol et al. |
| 9,022,984 B2 | 5/2015 | Ziebol et al. |
| 9,072,868 B2 | 7/2015 | Ziebol et al. |
| 9,078,992 B2 | 7/2015 | Ziebol et al. |
| 9,352,142 B2 | 5/2016 | Ziebol et al. |
| 2004/0034329 A1* | 2/2004 | Mankus .............. A61M 25/00 604/500 |
| 2004/0156908 A1 | 8/2004 | Polaschegg et al. |
| 2005/0124970 A1* | 6/2005 | Kunin .............. A61M 39/162 604/508 |
| 2005/0171493 A1 | 8/2005 | Nicholls |
| 2005/0220882 A1 | 10/2005 | Pritchard |
| 2005/0267421 A1 | 12/2005 | Wing |
| 2005/0288551 A1 | 12/2005 | Callister et al. |
| 2006/0024372 A1 | 2/2006 | Utterberg et al. |
| 2006/0206178 A1 | 9/2006 | Kim |
| 2008/0132880 A1 | 6/2008 | Buchman |
| 2008/0172007 A1 | 7/2008 | Bousquet |
| 2008/0319423 A1 | 12/2008 | Tanghoj et al. |
| 2009/0062766 A1* | 3/2009 | Howlett .............. A61M 39/165 604/411 |
| 2009/0137969 A1 | 5/2009 | Colantonio et al. |
| 2009/0205151 A1 | 8/2009 | Fisher et al. |
| 2009/0247485 A1 | 10/2009 | Ahmed et al. |
| 2010/0106102 A1 | 4/2010 | Ziebol et al. |
| 2010/0106103 A1 | 4/2010 | Ziebol et al. |
| 2010/0143427 A1* | 6/2010 | King ..................... A01N 25/34 424/405 |
| 2011/0030726 A1 | 2/2011 | Vaillancourt et al. |
| 2013/0039953 A1* | 2/2013 | Dudnyk .............. A61L 27/34 424/400 |
| 2013/0144258 A1 | 6/2013 | Ziebol et al. |
| 2013/0204231 A1 | 8/2013 | Ziebol et al. |
| 2013/0274686 A1 | 10/2013 | Ziebol et al. |
| 2015/0343174 A1 | 12/2015 | Ziebol et al. |
| 2016/0001058 A1 | 1/2016 | Ziebol et al. |

FOREIGN PATENT DOCUMENTS

| | | |
|---|---|---|
| EP | 1442753 | 2/2007 |
| EP | 1813293 | 8/2007 |
| WO | 2006102756 | 10/2006 |
| WO | 2010062589 | 7/2010 |
| WO | 2013009998 | 1/2013 |

OTHER PUBLICATIONS

File History from related U.S. Appl. No. 12/605,966, downloaded Jun. 3, 2015, 246 pages.

File History from related U.S. Appl. No. 13/752,385, downloaded Jun. 3, 2015, 270 pages.

File History from related U.S. Appl. No. 13/834,755, downloaded Jun. 3, 2015, 247 pages.

File History from related U.S. Appl. No. 13/915,605, downloaded Jun. 3, 2015, 302 pages.

Response to Communication Pursuant to Article 94(3) EPC for European Patent Application No. 098295876, dated Nov. 29, 2012 and filed with the EPO Mar. 18, 2013, 7 pages.

Final Office Action, dated Oct. 22, 2012 in U.S. Appl. No. 12/605,963, "Apparatus for Delivery of Device and Antimicrobial Agent Into Trans-Dermal Catheter," (11 pages).

Final Office Action, dated Oct. 18, 2012 in U.S. Appl. No. 12/605,966, "Device for Delivery of Antimicrobial Agent Into Trans-Dermal Catheter," (14 pages).

International Search Report and Written Opinion, for PCT/US2012/046496, dated Jan. 28, 2013, (12 pages).

Non-Final Office Action, dated Mar. 21, 2012 in co-pending U.S. Appl. No. 12/605,963, "Device for Delivery of Antimicrobial Agent Into Trans-Dermal Catheter," (11 pages).

Non-Final Office Action, dated Feb. 17, 2012 in co-pending U.S. Appl. No. 12/605,966, "Device for Delivery of Antimicrobial Agent Into Trans-Dermal Catheter," (11 pages).

Notification of First Office Action, dated Dec. 4, 2012, from Chinese Application No. 200980142920.4, based on PCT/US2009/062190 and priority U.S. Appl. No. 61/108,716, 9 pages.

PCT International Search Report and Written Opinion, from International Application No. PCT/US2009/062190, corresponding to U.S. Appl. No. 12/605,966, dated May 26, 2010, (11 pages).

Office Action Received, for European Application No. 09829587.6, dated Nov. 29, 2012 (5 pages).

PCT Notification Concerning Transmittal of International Preliminary Report on Patentability, From International Application No. PCT/US2009/062190, corresponding to U.S. Appl. No. 61/108,716, dated May 12, 2011, (6 pages).

Response to Final Office Action, dated Oct. 18, 2012, in co-pending U.S. Appl. No. 12/605,966, filed with USPTO Dec. 5, 2012 (6 pages).

Response to Final Office Action, dated Oct. 22, 2012, in co-pending U.S. Appl. No. 12/605,963, filed with USPTO Dec. 19, 2012 (8 pages).

Response to Non-Final Office Action, dated Feb. 17, 2012, in co-pending U.S. Appl. No. 12/605,966, filed with USPTO Jun. 18, 2012 (12 pages).

Response to Non-Final Office Action, dated Mar. 21, 2012, in co-pending U.S. Appl. No. 12/605,963, filed with USPTO Aug. 21, 2012 (6 pages).

Non Final Office Action for Chinese Patent Application No. 201280042898.8, dated May 21, 2015 (15 pages) with English Translation.

Final Office Action for U.S. Appl. No. 13/915,605, dated Dec. 27, 2013 (14 pages).

Amendment and Response After Final submitted on Feb. 27, 2014 for U.S. Appl. No. 13/915,605, (12 pages).

International Preliminary Report on Patentability for PCT/US2012/046496, dated Jan. 23, 2014 (8 pages).

(56) References Cited

OTHER PUBLICATIONS

Notice of Allowance for U.S. Appl. No. 13/752,385, dated Nov. 22, 2013 (12 pages).
Notice of Allowance for U.S. Appl. No. 13/834,755, dated Nov. 22, 2013 (12 pages).
Non-Final Office Action from U.S. Appl. No. 13/915,605, dated Aug. 29, 2013, 20 pages.
Non-Final Office Action from U.S. Appl. No. 13/752,385, dated Jun. 12, 2013, 25 pages.
Non-Final Office Action from U.S. Appl. No. 13/834,755, dated Jun. 20, 2013, 30 pages.
Non-Final Office Action for U.S. Appl. No. 14/720,378 dated Dec. 17, 2015 (28 pages).
Notice of Allowance for U.S. Appl. No. 14/720,378, dated Apr. 20, 2016 (11 pages).
Second Office Action for Chinese Patent Application No. 201280042898.8, dated Apr. 5, 2016 (11 pages) with English translation.
Extended European Search Report for European Patent Application No. 12810890.9 dated Dec. 9, 2015 (11 pages).

* cited by examiner

METHOD OF DELIVERING ANTIMICROBIAL TO A CATHETER

This application claims the benefit of U.S. Provisional Application No. 61/506,979, filed Jul. 12, 2011, the contents of which are herein incorporated by reference.

FIELD OF THE INVENTION

The present invention relates to medical devices for preventing infectious organisms from entering and occupying the lumen of catheters and drainage tubes, and more particularly, to systems, methods, and articles for delivering antimicrobial agents into the lumen and near the entry region (at the proximal end) of catheters and drainage tubes.

BACKGROUND OF THE INVENTION

Hemodialysis catheters allow patients with renal disease to have toxins removed from their bloodstream. Without the use of catheters, many of these patients would not survive. However, long-term hemodialysis catheters have a serious drawback in that a significant percentage of catheters fail due to infection, resulting in elevated mortality rates and large annual healthcare costs associated with treatment. Furthermore, bloodstream infections are a leading cause of death in the United States, and many of those infections are attributable to vascular access devices such as hemodialysis catheters. The mortality rate associated with such infections is considerable.

Therefore, a need exists for a manner in which infections relating to long-term hemodialysis catheters can be reduced.

SUMMARY OF THE INVENTION

The present application is directed, in part, to a device for delivering an antimicrobial agent into the lumen of a transdermal catheter. The device comprises an elongate member configured for insertion into the proximal end of a catheter and an antimicrobial composition positioned to be delivered into the catheter. At least a portion of the antimicrobial composition is delivered to the exterior of the proximal end of the catheter upon insertion of the elongate member into the proximal end of the catheter.

The application is also directed to a device for delivering an antimicrobial agent into the lumen of a trans-dermal catheter, the device comprising a capping member configured for placement over the proximal end of a catheter; and an antimicrobial composition positioned on the interior of the capping member.

The application is further directed to a method of applying an antimicrobial to the proximal end of a trans-dermal catheter. The method includes providing a transdermal catheter; filling at least a portion of the proximal end of the transdermal catheter with a lock solution; clamping the transdermal catheter near its proximal end to restrict flow of the lock solution into the distal end of the transdermal catheter; and inserting an elongate member into the proximal end of the transdermal catheter such that the elongate member sufficiently displaces lock solution so as to have the lock solution flow from the proximal end of the catheter. The elongate member includes or incorporates an antimicrobial material.

This summary is not intended to be limiting of the invention. The invention is further described in the following detailed description and claims.

BRIEF DESCRIPTION OF THE DRAWINGS

The invention may be more completely understood in connection with the following drawings, in which.

DETAILED DESCRIPTION OF THE INVENTION

Figure 1A:
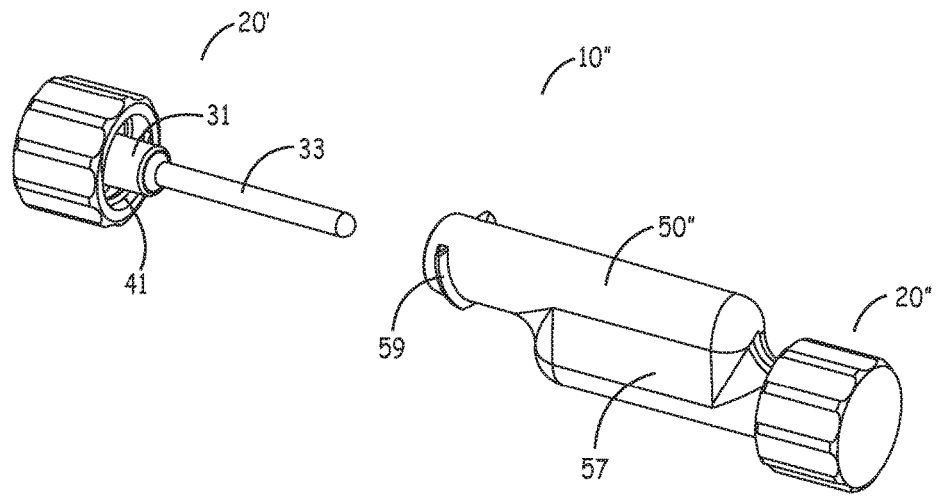
FIG. 1A is a perspective view of a dual-shield with two caps made in accordance with the preferred implementation of the invention. One cap is inserted into the dual shield; the other cap is not inserted.

The present invention relates to devices, systems, and methods for treating, preventing and eliminating infectious organisms in medical devices, such as catheters and drainage tubes, and preventing the organisms from entering the bloodstream. The devices, systems, and methods deliver antimicrobial agents into the lumen and near the entry region of catheters and drainage tubes. The following detailed description presents a description of certain specific embodiments to assist in understanding the claims. However, one may practice the present invention in a multitude of different embodiments as defined and covered by the claims.

The present invention includes, in certain implementations, methods and devices for preventing organism proliferation and biofilm formation in catheters so that organisms aren't able to exit the catheter and enter the bloodstream of a patient. The device and system prevents, or reduces the number of, organisms reaching the bloodstream by employing any or all of the following three prevention methods: 1) physically blocking migration of organisms outside the catheter, 2) killing organisms along the threads, end face and luer connector at the proximal end (outside of the body) of the catheter using an antimicrobial, and/or 3) killing organisms within a confined region of the catheter using an antimicrobial agent and/or a physical barrier in the catheter lumen. A fourth mode of action, scrubbing the catheter wall (to physically remove organisms adhered to the catheter's proximal end (thread and/or end face) and/or the interior wall section upon removing the cap from the catheter) may also be used in conjunction with the other methods and devices, or independently in certain implementations.

In a first aspect, the present invention includes an organism barrier at the external end of the catheter, also referred to herein as the proximal end of the catheter. This barrier provides a seal to keep organisms from reaching the end face and luer portions of the connector on a catheter. This can be accomplished, for example, by using either of the following features: First, placing an elastomeric flap or gasket (i.e., silicone, neoprene, polyurethane, etc.) that is positioned at the end of the cap's connector or, alternatively, along the inner wall of the cap's locking-ring. The flap preferably makes a fluid tight seal against the outer wall of the catheter's connector, thereby decreasing the likelihood of microbial incursion and preventing microbial growth. Second, placing foam, either closed cell or open cell that preferably contains an antimicrobial, along the inner wall of the cap's retaining ring and/or at the most proximal location in the cap such that it will abut and seal against the proximal end of the catheter's connector surface (also called the end face).

An embodiment using an antimicrobial agent along the cap's tread region, but not containing an organism barrier, can also be used to reduce the number of organisms that can enter the catheter. This reduction in the number of organisms that can enter the catheter is accomplished by killing organisms within the tread and end face region. The cap is optionally designed to transfer antimicrobial agent from the cap to the catheter threads. This is accomplished by displacing fluid from the catheter into the thread region of the connector. The elongate member and luer, when entering the catheter, displace the catheter's fluid, causing the fluid to flow out into the thread region between the connector and the cap. Antimicrobial agent dissolves in the fluid, causing the fluid to become saturated with antimicrobial agent. The antimicrobial fluid produces an effective antiseptic region, killing organisms on the connector. Furthermore, as the fluid dries, antimicrobial precipitates from the fluid and is deposited onto the catheter threads and end face. This process is repeated every time a new cap is placed onto the catheter, thus replenishing the antimicrobial agent on the catheter's proximal region with every new cap.

In a second aspect, the invention is directed to adding of an antimicrobial along a luer connector. This can be accomplished, for example, by coating a male luer connector with various antimicrobial agents.

In a third aspect, the invention is directed to an antimicrobial agent inside the catheter. The antimicrobial can be delivered as a coating that elutes from a coated elongate member, that is coated on (or impregnated into) a elongate member (such as 250 μg of chlorhexidine acetate in a layer approximately 2 μm thick along a 17 mm long×1.9 mm diameter elongate member/rod). The elongate member has the added benefit of displacing fluid from within the catheter as it is inserted, thereby transferring the solution to the outer proximal region of the catheter connector (end face and treads). Antimicrobial agent from the cap dissolves into the displaced fluid, and thereby disinfecting the proximal end of the connector. Furthermore, when the fluid dries, it deposits a coating of chlorhexidine acetate or other appropriate antimicrobial on the connector as described above. As an alternative to using the elongate member, the chlorhexidine acetate or other antimicrobial agent may be delivered by a coating on a luer tip (such as 250 μg of chlorhexidine acetate in a layer that is approximately 20 μm thick). A minimum of 10 μg of chlorhexidine acetate on the elongate member is effective for many organisms in some implementations. A desirable minimum of greater than 100 μg is effective for most organisms, and a further desired minimum of 250 μg is highly effective against all of the major organisms.

Types of antimicrobial agent can include chlorhexidine base, chlorhexidine acetate, chlorhexidine gluconate, EDTA, silver sulfadiazine, or Taurolidine; or combinations thereof. Other antimicrobial agents may also be used. Chlorhexidine acetate is preferred because it has a long history of human use, with a well understood safety and efficacy profile.

Typically these methods are also used in conjunction with confinement of the antimicrobial in the catheter, such as by relying on a catheter clamp to confine the antimicrobial agent in a portion of the proximal end of the catheter (that portion of the catheter outside of a patient and in particular that portion nearest the connector on the catheter by which fluids enter and leave the catheter). Extension tube clamps are part of each hemodialysis catheter and are currently used to confine lock solutions that are used to help ensure catheter patency. Using the existing clamp methodology, the risk of air embolus and lock solution entering the patient is very small and consistent with the current state of the art for conducting hemodialysis procedures. In other medical devices, such as catheters that do not possess catheter clamps, a swellable cap tip or other confinement technique, such as those described in United States patent application publication number US 2010/0106103 A1, may be used.

Organism mechanical removal can also be utilized. In this regard, a portion of the elongate member can scrap the catheter wall upon removal, such as by having ribs incorporated into the elongate member. In some implementations, after placing the elongate member into the catheter, anisotropic swelling moves ribs (or other projections) against wall, which provides a tighter fit against the wall after swelling and further promotes mechanical removal of the organisms. Also, it is possible for the tip of the elongate member to swell (or other portions such as ribs to swell), or swelling along the length of the elongate member. Preferably the elongate member's unswollen diameter is smaller than the catheter lumen when the elongate member is being inserted, but swells to conform to the inner shape (or larger) of the catheter lumen to enhance the mechanical removal of the organisms during removal. Various polyurethanes or other material may be used to produce suitable anisotropic swelling and mechanical stability; more specifically, Lubrizol 1065D is suitable for a non-swelling elongate member and TG-500 is suitable for an anisotropic swelling (or isotropic swelling) tip which may be bonded with each other using heat bonding or other suitable methods.

An embodiment of the invention, herein referred to as "the cap", contains an elongate member that can be inserted into a medical device, such as a catheter or a drainage tube, for the prevention and treatment of infectious organisms within the medical device and in proximity to the elongate member, and further prevents the migration of infectious organisms into the body by providing an antimicrobial and/or physical barrier. For the sake of simplicity, the term "catheter" is used for all medical devices in which the present invention can be inserted and used to treat, prevent, and eliminate infectious organisms. The cap may be removed from the catheter to allow the catheter to be used in a dialysis procedure or other procedure. After the procedure is complete, a new cap may be used to seal and protect the catheter. The removal of one cap and the replacement with a new cap may be repeated an indefinite number of times. With each new cap, the antimicrobial agent inside and outside of the catheter is reestablished. Another aspect of the invention is that antimicrobial agent is transferred from the cap to the catheter with each use.

An example embodiment includes an elongated rod comprising a suitable material into which an antimicrobial agent has been incorporated. The term "antimicrobial," as used here, includes any substance or substances that kills or inhibits the growth of organisms such as bacteria, fungi, protozoa, viruses, etc. It should also be noted that there can be one or more antimicrobial agents used. Therefore, throughout this document, antimicrobial agent refers to one or more antimicrobial agents. While the invention may be used in a variety of medical devices, a catheter, and more specifically a long-term hemodialysis catheter, will be used to describe the use of the invention. The use of these examples is not meant to confine or limit the use of the invention in other types of catheters or medical devices, such as peritoneal dialysis catheters, urinary catheters, PICC lines, central venous catheters, feeding tubes and drainage catheters.

One useful application of the invention is in preventing infections in people with hemodialysis catheters. The present invention prevents or eliminates infectious organisms on connector and the luminal wall of a catheter by providing a means for the prolonged presence of an antimicrobial agent and/or providing a means for periodically scrubbing the luminal wall of the catheter to remove the biofilm in which infectious organisms proliferate.

Competing methods for preventing, eliminating, and treating infectious organisms in the lumen of a catheter are in limited use. One method uses an antimicrobial coating on or in the internal wall of the catheter. The issues that have precluded widespread use include the antimicrobial coating eventually wearing off, losing potency, or becoming covered with blood products, rendering the coating ineffective. When antibiotics are used as the antimicrobial agent, there is an additional concern regarding the emergence of resistant organisms to antibiotics and the risk of anaphylaxis to the antibiotics. Another method for treating infectious organisms in the lumen is the use of an antibiotic or antimicrobial liquid, known as a locking agent or locking solution. In this method, an antimicrobial fluid is injected into the catheter, and a cap is attached to the hub of the catheter to prevent the fluid from leaking out of the catheter and to prevent infectious organisms from entering into the lumen.

One issue precluding widespread use of this method is concern for the emergence of resistant organisms if an antibiotic agent is used. This concern may be virtually eliminated, however, by using a non-antibiotic antimicrobial, such as taurolidine. Another issue when dialysis catheters are filled with locking solutions is that the locking solution spills into the bloodstream. This occurs for two reasons. First, when the catheter is filled with a volume equal to the catheter volume, a significant portion of the fluid leaks out due to the nature of the laminar flow profile in the catheter. Second, blood flow by the tip/distal end results in the injected catheter locking solution being pulled out due to the Venturi effect, and density differences between the lock solution result in spillage of the solution into the bloodstream. It has been reported that 60% or more of the locking solution is spilled into the bloodstream in the first few hours after instillation. Accidental overdosing, either from injecting too much volume or too high of concentration of the locking solution, can cause additional spillage into the bloodstream. Spillage has resulted in adverse events, including death. For instance, spillage has resulted in death from transient hypocalcemia when a citrate solution was used. In addition, other adverse events may occur as some types of locking solutions may build up in the body.

In the case of using the cap with dialysis catheters, the present invention is designed to be replaced regularly after each dialysis session, approximately three times per week. This replenishes the antimicrobial agent with each replacement, resulting in a consistent and high concentration of antimicrobial agent present within and upon the catheter on an ongoing basis resulting in decreased risk of infection. However, the confinement method, such as clamps, as used in conjunction with the invention, prevents a significant amount of antimicrobial agent from leaking into the bloodstream on a regular basis.

In addition, separation between the antimicrobial agent and blood can result in lower infection rate, fewer side effects, and less risk of developing resistant bacteria because a non-antibiotic antimicrobial is used. In certain embodiments, the present invention creates a physical barrier between the blood and the antimicrobial agent. The barrier greatly reduces the exchange of antimicrobial agent with blood circulating in the body, resulting in fewer side effects from the antimicrobial agent. This can result in a more consistent level of antimicrobial agent along the length of the catheter adjacent to the cap. Additionally, the barrier reduces the amount of antimicrobial agent entering the bloodstream, thus reducing the risk of an adverse reaction to the agent or developing organisms resistant to the antimicrobial agent. In comparison, it is well-known that liquid locking agents can and do routinely migrate into the bloodstream, and the blood can migrate into the catheter, thus reducing the effectiveness of the antimicrobial agent, increasing the possibility of bacteria entering the bloodstream and increasing the rate of thrombosis in the catheter. The act of flushing the catheter lumen with a fluid agent into the lumen will result in the removal of blood from the lumen and thus reduce the risk of thrombosis. If the liquid agent is an anti-thrombotic lock, such as heparinized saline or saline with 4% sodium citrate, the risk of thrombosis is further reduced. The use of a confinement means, as described in the present invention as a swellable elongate member tip, swellable elongate member, or catheter clamp, prevents the blood from reentering the lumen and results in a lower risk of thrombosis in the lumen.

A further aspect of the invention relates to protecting the caps from contamination prior to use and during handling in order to keep the elongate member and luer sterile prior to insertion into the catheter. A shield over the elongate member and luer may be used. A standard shield, which protects one luer and elongate member, is suitable for keeping one elongate member and luer sterile. A novel shield is hereafter described which improves handling while maintaining sterility protection, and facilitates low-cost injection molding. The novel shield holds two caps within one shield body, where the two caps are held 180 degrees opposed in an axially offset manner with at least a portion of the two elongate members axially overlapping one another, with a physical barrier between the two caps. The shield may have threads to provide a means for removably attaching the caps to the shield. This novel configuration allows the user to hold one piece rather than two, thus easing handling and decreasing the risk of dropping the caps. The barrier between the two caps ensures that, when one cap is removed from the shield, that the other cap remains sterile. The caps, secured within the shield, may be packaged in a pouch using a suitable packaging material, such as a metal film with a polymer laminate to facilitate heat sealing. The metal layer is useful to minimize adverse effects of humidity. The device, inside the pouch, may be sterilized using gamma radiation or other suitable sterilization method. Gamma radiation has the advantage of effectively sterilizing the product while it is contained within moisture-proof packaging.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

Research and development into preventing catheter-related bloodstream infections (CRBSI) over the last twenty years has been focused on methods for killing the bacteria along the inside and outside length of the catheter. This research has resulted in success at reducing the incidence of CRBSI in some catheter types. For instance, commercially successful antimicrobial coated catheters have resulted in a decrease in the incidence of infection in applications that use short-term (non-tunneled) catheters. However, these coating wash off with use and therefore are not effective for long-term applications. The use of long-term (tunneled, cuffed) hemodialysis catheters result in approximately 2.3 bloodstream infections every 1000 catheter days. Said another way, a patient dialyzing with a hemodialysis catheter can expect to develop a bloodstream infection, on average, every 14 months. To fix this remaining problem, much of today's research is focusing on ways to eliminate biofilm within catheters and on ways to produce longer lasting antimicrobial coatings that are capable of killing organisms within catheters.

Infectious organisms typically colonize a catheter in three distinct ways. First, the infectious organisms may colonize the catheter by traveling in the bloodstream and eventually adhering to the catheter. This form of transmission is believed to be rare. Second, the infectious organisms may colonize the catheter by traveling along the outer wall of the catheter after entering at the catheter's body exit site. This method of infection transmission has been greatly reduced by tunneling the catheter under the skin for several centimeters, and by the addition of a cuff on the outer wall of the catheter. Body tissue grows into the cuff and creates a barrier for infection. Third, the infectious organisms may colonize the inner lumen of the catheter, entering at the hub and/or adaptor of the catheter connector, eventually migrating down the lumen of the catheter to the bloodstream. This method of infection transmission is a leading cause of bloodstream infections in patients with long-term indwelling catheters. Therefore, a need exists for improved devices, systems, and methods for eliminating, treating, and preventing such contamination.

The present invention prevents, reduces and can even eliminate infectious organisms from the entry region of a catheter or tube, and from within the inner luminal surface of a catheter or other similar medical devices by providing a means for the prolonged presence of an antimicrobial agent and/or providing a means for periodically scrubbing the entry region and/or lumen of the catheter or other medical device to remove the infectious organisms and the biofilm in which infectious organisms proliferate.

The present invention includes methods and devices for killing organisms and preventing organism proliferation and biofilm formation in catheters so that organisms aren't able to exit the catheter and enter the bloodstream of a patient. The article of the present invention prevents, or reduces the number of, organisms reaching the bloodstream by employing any or all of the following three prevention methods: 1) physically blocking migration of organism outside the catheter, 2) killing organisms along the threads, end face and luer connector (inside and outside of the connector) at the proximal end (outside of the body) of the catheter using an antimicrobial, and/or 3) killing organisms within a confined region of the catheter using an antimicrobial agent and/or a physical barrier in the catheter lumen. A fourth mode of action, scrubbing the catheter wall (to physically remove organisms adhered to the interior wall section upon removing the cap from the catheter) may also be used in conjunction with the other methods and devices.

As noted above, the invention is directed in part to an antimicrobial agent inside the catheter. The antimicrobial agent can be delivered as a coating that elutes from a coated elongate member, that is coated on, or impregnated into, an elongate member (such as 250 µg of chlorhexidine acetate in a layer approximately 2 µm thick along a 17 mm long×1.9 mm diameter elongate member/rod). The elongate member has the added benefit of displacing fluid from within the catheter as it is inserted, transferring the solution to the outer proximal region of the catheter connector (end face and treads). Antimicrobial agent from the cap dissolves into the displaced fluid, and thereby disinfecting the proximal end of the connector. Furthermore, when the fluid dries, it deposits a coating of chlorhexidine acetate or other appropriate antimicrobial on the connector as described above. As an alternative to using the elongate member, chlorhexidine acetate or other antimicrobial agent may be delivered by a coating on a luer tip (such as 250 µg of chlorhexidine acetate in a layer that is approximately 20 µm thick). The luer portion is also coated with an antimicrobial agent (such as 50 µg of chlorhexidine acetate in a layer that is approximately 0.4 µm thick). It is also possible to inject an antimicrobial agent into the catheter using a syringe, or to deliver antimicrobial agents by way of the connector tip cavity (dry dissolvable amount, applicable for Citrate or others requiring large amounts of antimicrobial agent).

Referring now to the figures, example implementations of the invention are shown. FIG. 1A shows an exploded view of a dual shield system 10" that includes an arterial cap 20', a venous cap 20" and a shield 50"; the colors are typically chosen to match the standard colors used in hemodialysis: red for the arterial cap 20' and blue for the venous cap 20". The dual shield system 10" contains two caps within the same shield 50". The shield 50" provides for easier handling because there are fewer parts to handle and hold. The dual shield system 10" is packaged within a heat-sealed foil-pouch (not shown) and gamma sterilized. The foil-pouch is opened at the clinic immediately before use of the caps. The cap threads 41 removably engage the dual shield threads 59 to allow easy removal of the caps 20', 20" from the shield 50". The flattened side 57 creates a convenient means for gripping the shield as the caps 20', 20" are removed. In addition, the flattened side 57 disrupts the rotational symmetry of the shield 50", thus making the shield system 10" resistant to rolling onto the floor or being dropped.

Figure 1B:
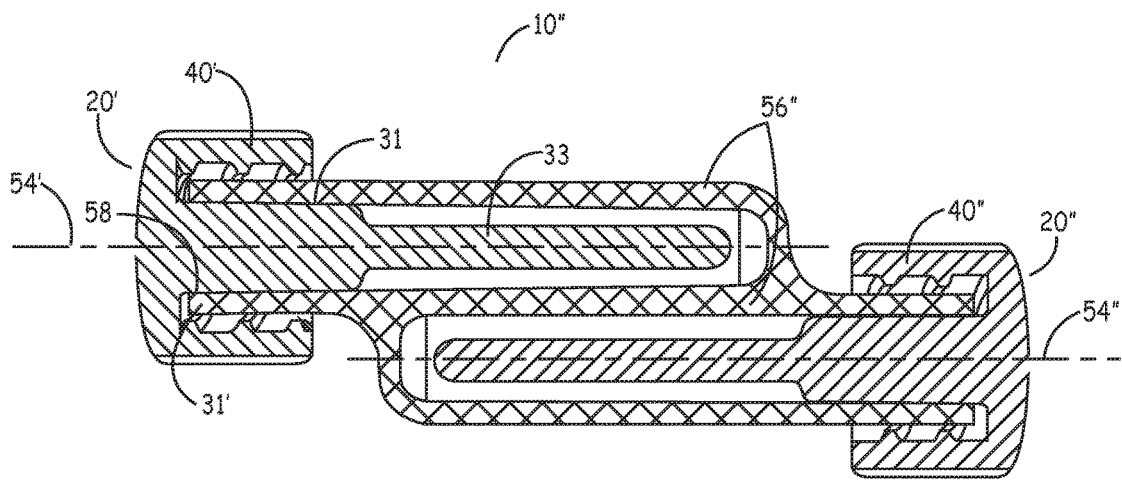
FIG. 1B is a side cross section view of two caps inserted into a dual-shield and is made in accordance with the preferred implementation of the invention.

FIG. 1B shows a cross section of a dual shield system 10" with an arterial cap 20' and a venous cap 20" each inserted into a shield 50". The shield 50" is designed to keep the caps 20', 20" axially offset as shown by the arterial cap axis 54' and the venous cap axis 54". The offset axis is advantageous over a coaxial design because it decreases the length of the system 10", allowing it to fit into a shorter pouch and making it easier to handle. In addition, the caps 20', 20" are 180 degrees opposed from each other, thus making the retaining rings 40', 40" physically separated from one another. This is makes the retaining rings 40', 40" easier to grasp because the arterial retaining ring 40' does not physically block finger access to the venous retaining ring 40", and vice versa. The shield 50" provides protection to the caps 20', 20" and further aids maintenance of sterility prior to use because each of the caps 20', 20" are separated by a wall 56". In an example embodiment, the most proximal portion 31' of the male luer 31 contacts the receiving edge 58 of the dual shield 50" such that the most proximal portion 31' forms a tapered sealing member. The rest of the male lure 31 does not contact the wall 56", and thereby minimizes the risk of removing the antimicrobial coating on the male luer 31. Typically the elongate member 33 also does not contact the wall 56" so as to minimize the risk of removing the antimicrobial coating.

Figure 2A:
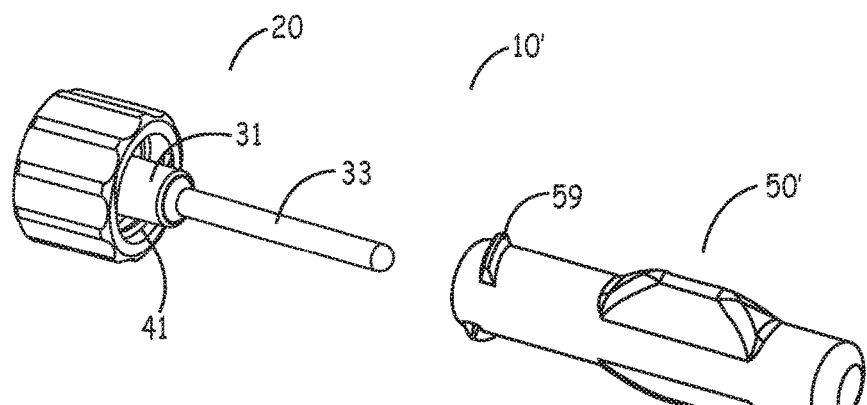
FIG. 2A is a perspective view of an elongate member and mono shield made in accordance with an implementation of the invention. The cap is shown not inserted into the mono shield.

FIG. 2A shows a perspective view of a mono shield system 10' with a cap 20, and a shield 50'. The shield 50' contains one cap within the housing. The mono shield system 10' is packaged within a heat-sealed foil-pouch (not shown) and gamma sterilized. The foil-pouch is opened at the clinic immediately before use of the cap. The cap threads 41 removably engage the mono shield threads 59 to allow easy removal of the cap 20 from the mono shield 50'.

Figure 2B:
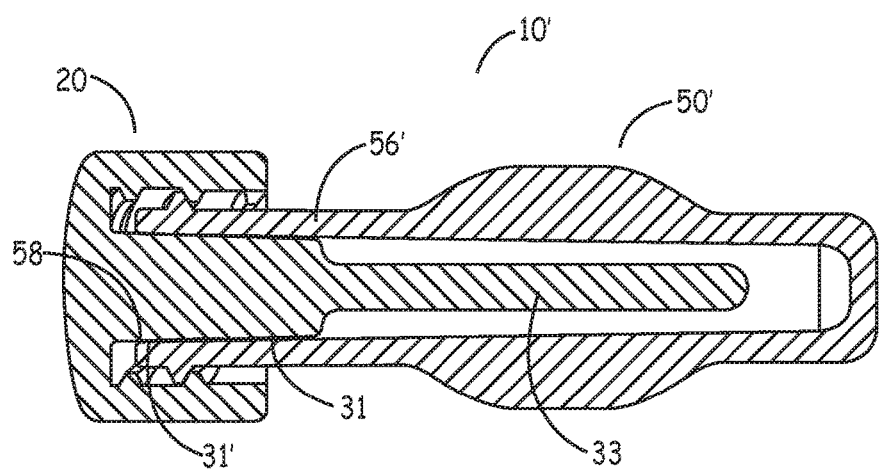
FIG. 2B is a side cross section view of a cap inserted into a mono shield made in accordance with an implementation of the invention.

FIG. 2B shows a cross sectional view of a mono shield system 10' with a cap 20 inserted into a mono shield 50'. The mono shield 50' provides protection to the cap 20 and further ensures that sterility is maintained prior to use. This is accomplished by enclosing the cap 20 by a wall 56". In an example embodiment, the most proximal portion 31' of the male luer 31 contacts the receiving edge 58 of the mono shield 50'; and in such embodiment the most proximal portion 31' forms a tapered sealing member. The rest of the male lure 31 does not contact the wall 56', and thereby minimizes the risk of removing the antimicrobial coating on the male luer 31. The elongate member 33 also preferably does not contact the wall 56' in order to minimize the risk of removing the antimicrobial coating.

Figure 3A:
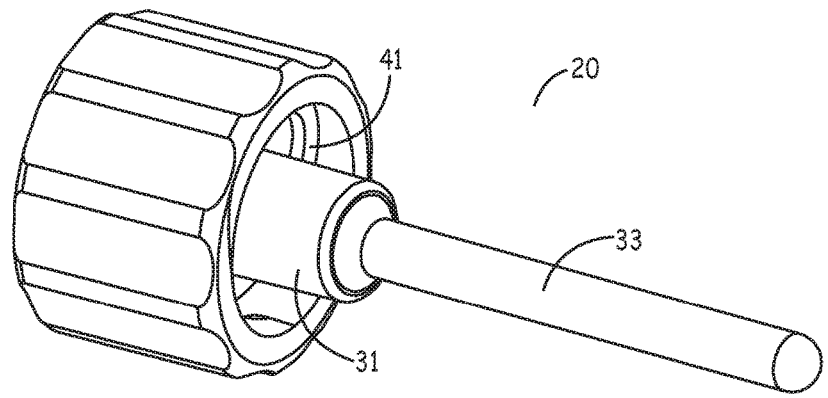
FIG. 3A is a perspective view, looking from the distal end of a cap, made in accordance with the preferred implementation of the invention.

FIG. 3A shows a cap 20 made in accordance with an example implementation of the invention. The cap 20 can be injected molded as a single unit out of a thermoplastic polymer resin to allow high volume production at low manufacturing costs. Suitable polymer will produce a durable part such that the elongate member 33 may be bent without breaking. Polymers with a minimum elongation at break of 100% are preferred. In addition, the polymer will typically allow a solvent (which is used in the antimicrobial coating process) to wet the surface evenly until the solvent evaporates, and the antimicrobial agent should adhere well to the surface such that the coating does not flake or fall off during handling. Various polymer materials may be used that meet these requirements, such as polyester, nylon, polyetherimide, polypropylene, polyvinyl chloride or other similar materials. Alternatively, the elongate member 33 may be manufactured using a dissolvable material which is impregnated with an antimicrobial agent, thus the antimicrobial is released into the solution when the elongate member 33 dissolves.

Portions of the cap 20 are typically coated and/or impregnated with an antimicrobial agent. In one embodiment, the antimicrobial agent is applied as a coating, with different amounts optionally applied to the elongate member 33, the male luer 31, and the cap threads 41. The antimicrobial agent can also be incorporated within the bulk polymer material, but coating the surface is preferred because surface coatings can generally be released into solution more rapidly than bulk agents; additionally surface coatings tend to require less overall antimicrobial agent than bulk agents because the antimicrobial agent on the surface is more readily dissolved. In some implementations a combination of surface coatings and incorporation into bulk polymer materials is used.

Suitable methods of coating the cap 20 are spraying and dipping, with spray coating being desirable because the amount of antimicrobial agent applied to each region (elongate member 33, male luer 33, and cap threads 41) can more easily be adjusted without affecting the amount located on other regions.

Figure 3B:
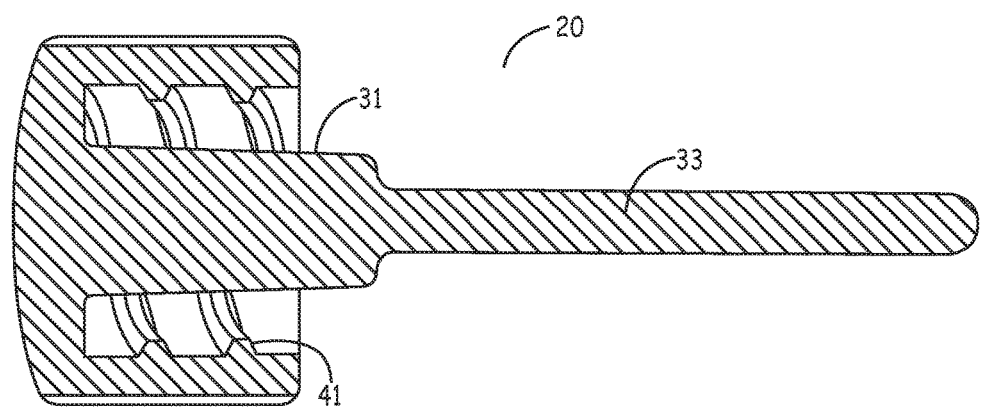
FIG. 3B is a side cross section view of a cap made in accordance with the preferred implementation of the invention.

FIG. 3B shows a cross section of a cap 20 made in accordance with an embodiment of the invention. The length and diameter of the elongate member 33 is sized to fit into a medical device. In the embodiment described herein, the catheter is a hemodialysis catheter. The male lure 31 and the cap threads 41 can be manufactured in accordance with the International Organization for Standardization standard ISO 594-2:1998(E) to be compatible with all hemodialysis catheters which are made according to the standard.

Figure 4A:
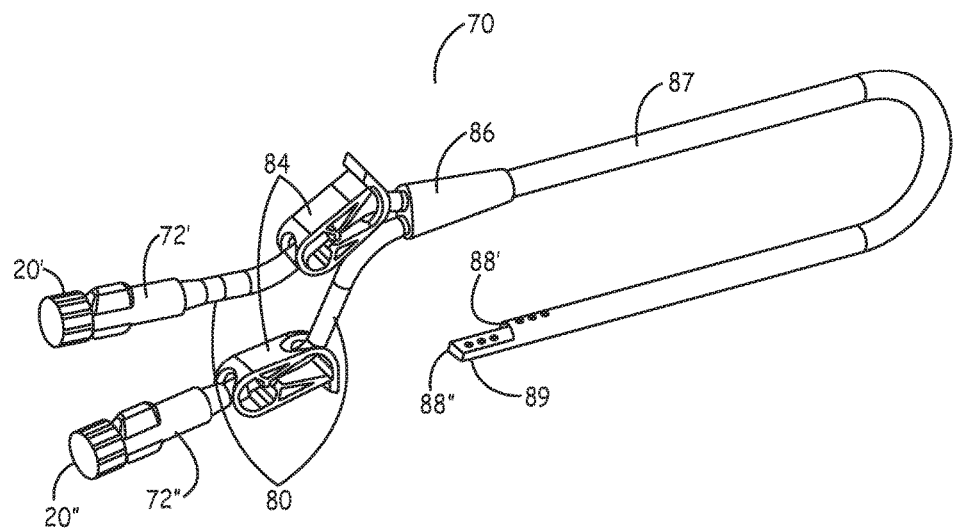
FIG. 4A is a perspective view of two caps made in accordance with the preferred implementation of the invention, and a catheter. The caps are shown inserted into the catheter.

FIG. 4A depicts a hemodialysis catheter 70 for use in conjunction with an embodiment of invention, and is shown with an arterial cap 20' in the arterial hub 72', and a venous cap 20" in the venous hub 72". When used with a hemodialysis patient, the two-lumen tube 87 is partially tunneled below the patient's skin, from the upper chest to the jugular vein. The two-lumen tube 72" enters the jugular vein and continues until the catheter tip 89 is in the region of the right atrium of the heart. The arterial lumen 88' runs inside the catheter 70 from the arterial hub 72' until exiting at the catheter tip 89. The venous lumen 88", similarly, runs inside the catheter 70 until it exits near the catheter tip 89. If bacteria or fungus are in either or both lumens 88', 88", these infection-causing organisms may enter the bloodstream and result in a systemic bloodstream infection, and therefore prevention of the entry and growth of microorganisms into the catheter 70 is important. The catheter contains a junction 86, where the extension tubes 80 transition from two tubes with two lumens into one tube with two lumens; the two lumens 88', 88" run the entire length of the catheter 70, from hub 72', 72" to catheter tip 89 without fluidly connecting with the other lumen. The arterial hub 72' is attached to the proximal end of one extension tube 80, and the venous hub 72" is attached to the proximal end of the other extension tube 80. In the depicted embodiment, a clamp 84 is positioned on each of the extension tubes 80, allowing the flow in the lumen to be blocked or opened. In practice, the clamps 84 are closed except during a dialysis session or other transferring of fluids within the catheter 70. The clamps 84 are typically repositioned each time the clamps 84 are opened in order to minimize the risk of damaging the extension tube 80 through multiple clamping in the same location.

Figure 4B:
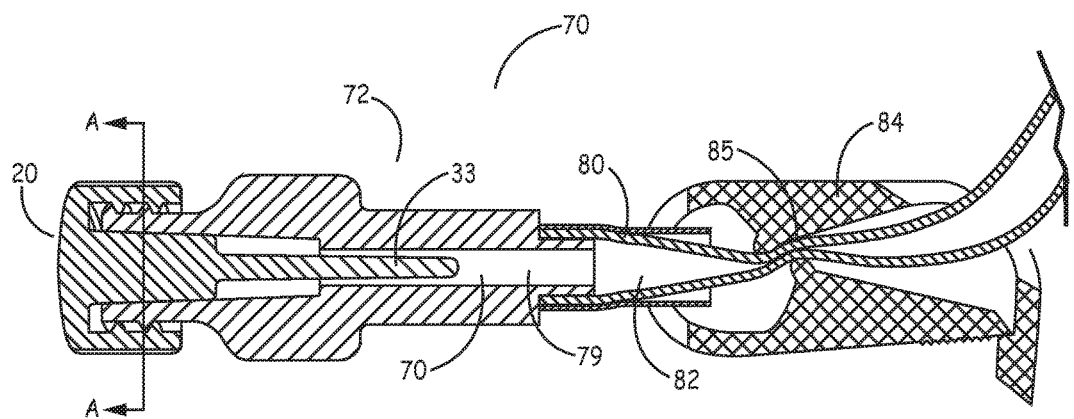
FIG. 4B is a side cross section view of a cap made in accordance with the preferred implementation of the invention, and inserted into a catheter.

In reference to FIG. 4B, the clamp 84 is shown located in close proximity to the hub 72. The clamp 84, when closed, creates a pinch point 85 which blocks the fluid flow in the lumen. Preferably the elongate member 33 will be short enough to ensure that the clamp 84 does not clamp onto the elongate member. In addition, the elongate member 33 must possess a small enough diameter to ensure that it can physically fit within the hub lumen 79. In embodiments where the elongate member 33 is long enough to enter the extension tube 80, the diameter of the extension tube must also fit within the extension tube lumen 82. The elongate member 33 should preferably be stiff enough to allow for insertion into the hub 72 without requiring sheaths, tubes or other insertion aids.

The surface area of the elongate member 33 should be large enough to allow for the desired amount of antimicrobial agent to be coated on the surface using spraying or dipping operations (or other application methods, including incorporation directly into the elongate member). The surface area is generally sized to produce an acceptable dissolution rate such that the antimicrobial agent enters the lock solution 90 at an acceptable rate and dosage. It is desirable for the antimicrobial agent to reach an effective level within an hour of the cap 20 being inserted into the catheter 70.

If the elongate member extends into the pinch point 85 of the clamp 84, it can potentially cause damage or leaking of the lock solution 90. Therefore the length of the elongate member 33 should be sufficiently short to ensure that it does not reach the pinch point 85 of the clamp 84. Suitable diameters for the elongate member 33 include 1.0 mm to 2.0 mm; and 1.7 mm to 1.9 mm. A suitable length includes less than 20 mm for the elongate member 33, alternatively less than 30 mm, less than 40 mm, or less than 10 mm. A particularly desirable length is 17 mm to 19 mm, but can vary for use with various catheters.

Figure 4C:
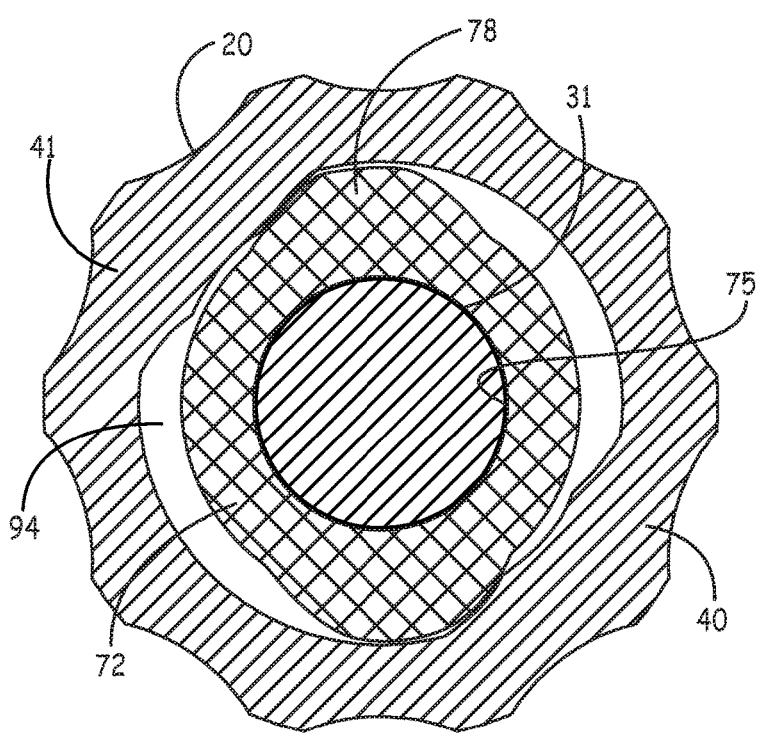
FIG. 4C is an end cross section view of a cap made in accordance with the preferred implementation of the invention, and inserted into a catheter.

In reference to FIG. 4C, an embodiment is depicted showing the end section view A-A as indicated in FIG. 4B, the cap 20 is shown fully inserted into the catheter hub 72. When fully inserted, the male luer 31 contacts the female luer 75 to create a fluid tight seal. The cap threads 41 engage the catheter threads 78 to retain the cap 20 on the hub 72. However, after the cap 20 is fully inserted into the hub 72, a void 94 is present between the retaining ring 40 and the hub 72. This void 94 can be a pathway for pathogenic organisms to travel along, thus allowing contamination of the hub surfaces with pathogenic organisms in the region between the retaining ring 40 and the hub 72. In order to reduce the incidence of catheter-related bloodstream infections, it is desirable to reduce or eliminate the number of pathogenic organisms in this region.

Figure 5A:
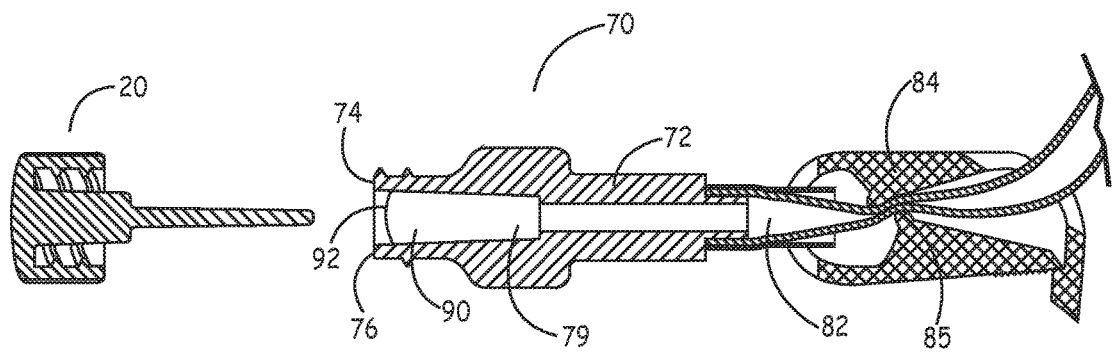
FIG. 5A is a side cross section view of a cap made in accordance with the preferred implementation of the invention, prior to cap being inserted into a catheter.
Figure 5B:
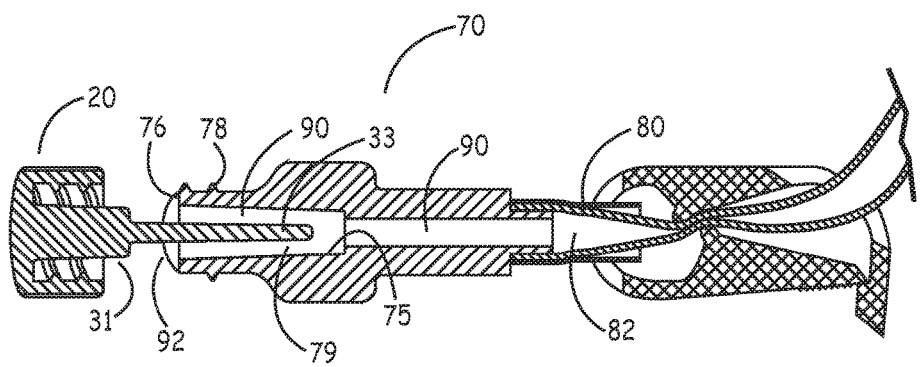
FIG. 5B is a side cross section view of a cap made in accordance with a preferred implementation of the invention, as the cap is being inserted into a catheter.
Figure 5C:
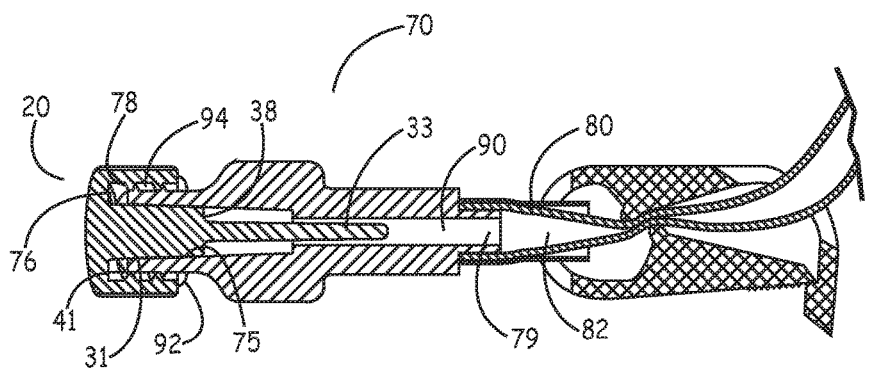
FIG. 5C is a side cross section view of a cap made in accordance with a preferred implementation of the invention, with the cap fully inserted into a catheter.

Referring now to FIG. 5A to 5C, various stages of installation of cap 20 are shown, wherein the insertion of the cap (with an elongate member) results in the flow of an antimicrobial containing liquid out the end of the catheter hub to kill microorganisms that would otherwise potentially intrude into the hub and then the catheter lumen. In FIG. 5A, the cap 20 is shown immediately prior to being inserted into the hub 72 of a catheter 70. Within the hub lumen 79 is a liquid locking solution 90, the most proximal portion of which forms a meniscus 92. The locking solution for hemodialysis catheters is most often heparinized saline (100 IU/ml to 5000 IU/ml of heparin), sodium citrate solution (typically 4% sodium citrate), or saline. Patient care technicians and nurses are trained to keep the meniscus 92 at the proximal end 74 of the hub 72. However, it is not unusual for the meniscus to fall several millimeters within the hub lumen 79. The antimicrobial agent must produce the desired effect in any of the standard lock solutions. In practice, the clamp 84 remains closed (producing a pinch point 85) unless fluids are being transferred through the catheter 70; this is standard practice because it decreases the risk of introducing an air embolus into the patient's bloodstream through catheter 70.

In reference to FIG. 5B, the elongate member 33 is shown partially inserted into the hub lumen 79. The elongate member 33 displaces lock solution 90, which results in the meniscus 92 being pushed out of the lumen 90 and onto the end face 76 of the hub 70. Eventually, as the cap 20 continues to be inserted, the meniscus 92 (and lock solution 79) will travel over the catheter threads 78.

Next, referring to FIG. 5C, the cap 20 is shown fully inserted into the catheter 70. In this embodiment, the meniscus 92 travels beyond the void 94, completely filling the void 94 with lock solution. The lock solution causes the antimicrobial agent to dissolve, resulting in a transfer of antimicrobial agent from one or more of the coated parts (the elongate member 33, the male luer 31, and cap threads 41) into the solution. In addition, insertion of the elongate member into the locking solution further causes a transfer of antimicrobial agent to the previously uncoated parts such as the wall defining the inner hub lumen 79 and extension lumen 82, the female luer 75, the end face 76, and the catheter threads 78. Within several hours the solution within the void 94 may dry. In this manner an antimicrobial coating becomes transferred to the catheter threads 78 and the end face 76, resulting in an enhanced ability to kill any organisms on the catheter threads 78 and the end face 76, even if the organisms contaminate the surfaces after the solution dries. In practice, the void is often times infiltrated with sweat that contains organisms. In this scenario the dried antimicrobial agent becomes hydrated by the sweat, killing organisms that may be present in the sweat. Furthermore, the catheter threads 78 and the end face 76 become replenished with antimicrobial agent every time a new cap 20 is inserted. In current practice, a new cap is used after every dialysis session. The ability of the cap 20 to replenish the antimicrobial agent on a catheter 70, into a targeted location with a high risk of serving as a microorganism source, overcomes a significant shortcoming of antimicrobial coated catheters in which the antimicrobial agent wears off with use or is only applied to the interior of the catheter. A desirable amount of antimicrobial agent on the catheter threads 78 is 20 µg to 2 mg, alternatively 200 µg to 1.5 mg, and desirably 500 µg to 1.2 mg of chlorhexidine acetate. However, it will be understood that different levels can also be achieved with success.

The male luer 31 makes contact with the female luer 75 to create a fluid tight seal. These parts are typically manufactured in accordance with the International Organization for Standardization standard ISO 594-2:1998(E) in order to ensure proper sealing and intermateability. However, the junction between the male luer 31 and the female luer 75 is not fluid tight along the entire length of the interface. Some manufacturers of medical device hubs intentionally manufacture their female luers such that the male luer contacts the female luer near the male luer end face. This is done in order to reduce the risk of the splitting the hub. However, the unintended consequence is that proximal end of the luer interface allows for the potential infiltration of organisms. Once the organisms are present, they may be pushed further into hub lumen 79 by current caps (or other devices) the next time a cap (or other device) is inserted. Once the organisms are within the hub lumen (distal to the male luer) they can multiply, resulting in planktonic and sessile organisms, and eventually a biofilm. This problem can be countered by placing an antimicrobial agent along the male luer 31. The antimicrobial agent kills organisms that may be or become present along the female luer 75 before the organisms have a chance to be pushed into the hub lumen 79 or further multiply. Even with these protective measures, there is still a possibility that some organisms can make it beyond the female luer 75. To overcome that potential shortcoming, the preferred embodiment also contains antimicrobial on the elongate member 33, which dissolves or elutes into the lock solution 90, to kill organisms in the hub lumen.

The minimum amount of antimicrobial agent on elongate member 33 was determined through laboratory testing in which elongate members were placed into catheters under a variety of lock solutions and challenge organisms. The type of lock solution was varied among saline, heparinized-saline, 4% sodium citrate solution, and human serum. A variety of challenge organisms were used, such as *Candida albicans, Pseudomonas aeruginosa, Staphylococcus aureus*, and *Escherichia coli*. Testing performed by the inventors showed a dose response; the more chlorhexidine acetate contained on the elongate member 33, the more organisms that are killed in the catheter 70.

The maximum amount of antimicrobial agent that is placed on each of the cap's surfaces was developed by first reviewing how much antimicrobial is safe for the patient and then comparing that to how much antimicrobial agent the patient can potentially be exposed to by each of the cap's 20 surfaces that contain antimicrobial agent (elongate member 33, male luer 31, and cap threads 41). The amount of antimicrobial that is safe for the patient was determined by reviewing published information on levels (especially bloodstream levels) that are generally regarded as safe for patients.

Testing was conducted in order to derive how much antimicrobial agent the patient can potentially be exposed to from cap 20. The testing was designed to determine the transfer efficiency of antimicrobial agent from each applicable component (elongate member 33, male luer 31, and cap threads 41) to the bloodstream. In order to determine the potential bloodstream level, consideration was given for potential patient exposure that could occur under a variety of conditions, including unusual use or misuse (such as injecting the lock solution into the patient's bloodstream instead of aspirating the solution). The potential patient exposure was determined for each component individually and for the entire cap 20.

The minimum amount of antimicrobial agent on the elongate member 33 is the amount required to obtain an acceptable reduction (also referred to as kill) of infection causing organisms. The volume of solution that the antimicrobial agent dissolves into is important to understand because the more solution that is present, the more dilute the antimicrobial agent can become. The confined volume of lock solution 90 within the lumen is defined by the location of the meniscus 92, the geometry of the hub lumen 79, the geometry of the extension lumen 82, and the location of the pinch point 85. Since each of these items may vary, there is a considerable range of confined fluid volumes that is possible. After accounting for the design variations of existing hemodialysis catheters, it is evident that the preferred embodiment needs to produce a therapeutic concentration of antimicrobial agent within a 0.7 ml volume. In one embodiment, the amount of chlorhexidine acetate on the elongate member 33 is greater is 10 µg to 5 mg. In an alternative embodiment, the amount of chlorhexidine acetate is 100 µg to 2 gm. In yet another embodiment, the elongate member contains 250 µg to 550 µg.

These embodiments can produce broad spectrum kill of the target organisms, yet result in a low enough dose of chlorhexidine acetate that, even if all of the lock solution containing chlorhexidine acetate is injected directly into the bloodstream, it will result in a bloodstream level that remains at safe levels.

Figure 6:
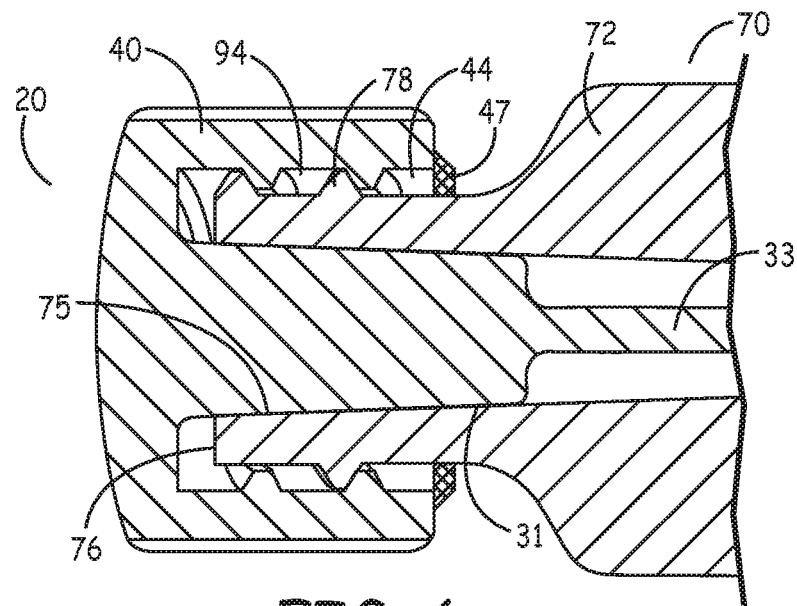
FIG. 6 is a side cross-section view of a cap with a seal at the distal end of the retaining ring made in accordance with an implementation of the invention, inserted into a catheter.

In reference to FIG. 6, a cap 20 is shown fully inserted into a catheter 70. This embodiment contains an end seal 47. The end seal 47 provides additional benefit by preventing organisms from entering the distal opening 44 thereby preventing the organisms from subsequently progressing through the void 94 where they could then contaminate the end face 76 and female luer 75. Reducing the number of organisms that can enter distal opening 44 can further reduce the incidence of CRBSI. The end seal 47 can be made of an elastic material so it is capable of stretching over the catheter threads 78 while the cap 20 is being inserted, and it should also conform to the shape of the hub 72 so it creates an effective organism-blocking seal. The end seal 47 is preferably made of a durable material so it does not rip or tear. It should be thin and flexible enough so it is easy to insert. The end seal 44 allows fluid to escape as the cap 20 is being inserted onto the catheter 70, yet acts as a barrier to substantially retain the lock solution that was pushed into the void 94 during insertion. In the preferred embodiment, this is accomplished by keeping the wall thin and flexible enough to allow the increased pressure to escape where the end seal 47 contacts the hub 72. In an example embodiment, the end seal 47 is over molded onto the retaining ring 40. A thermoplastic elastomer, such as Exxon Mobile's Santoprene, can be used. However, other materials, such as silicone, may be suitable. In an embodiment, the end seal 47 is in the range of 0.005 inch to 0.100 inch thick. In another embodiment, the end seal 47 is in the range of 0.010 inches to 0.040 inches thick.

The lock solution in void 94 also acts as a barrier to organism infiltration. It contains antimicrobial agent that has dissolved from the cap 20 surfaces (elongate member 33, male luer 31, and catheter threads 78). In a desired embodiment, the antimicrobial levels result in an antimicrobial concentration that is highly effectively at killing a broad spectrum of organisms.

Figure 7:
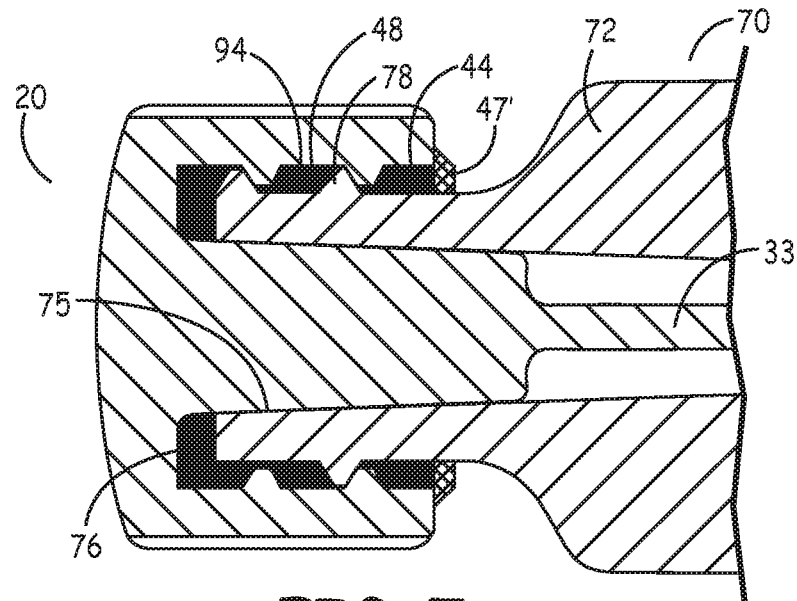
FIG. 7 is a side cross-section view of a cap with foam along the threads of the retaining ring made in accordance with an implementation of the invention, and inserted into a catheter.

In reference to FIG. 7, the cap 20 is shown fully in cross section inserted into a catheter 70. This embodiment can contain a thread seal 48 that is impregnated with an antimicrobial agent in the same amount as (and in place of) the amount on the cap threads 41 of FIG. 5C. The thread seal 48 provides additional benefit by preventing organisms from entering the distal opening 44 and, since the void 94 is now occupied with the thread seal 48, it prevents organisms from progressing through the occupied void 94 where they would otherwise contaminate the end face 76 and female luer 75. Reducing the number of organism that can enter distal opening 44 can further reduce the incidence of CRBSI. The thread seal 47' is preferably made of an elastic foam material that is capable of conforming around the catheter threads 78 while the cap 20 is being inserted, and it should also conform to the shape of the hub 72 so it creates an effective organism-blocking seal. The most distal end of the thread seal 47' often has a thin layer of closed polyurethane to help reduce evaporation of the solution. The thread seal 48 is desirably made of a durable material so it does not rip or tear. One aspect of the thread seal 48 is that it allows fluid to escape as the cap 20 is being inserted into the catheter 70, yet it acts as a barrier to substantially retain the lock solution that was pushed into the filled void 94 during insertion. In the preferred embodiment, this is accomplished by manufacturing the thread seal 48 out of an open cell hydrophilic medical polyurethane foam and having a thin layer of solid polyurethane at the most distal end of the thread seal 47'. The distal end of the thread seal 47' is desirably thin, such as 0.001 to 0.020 inch, and flexible enough to allow the increased pressure to escape where it contacts the hub 72. The thread seal 48 and the antimicrobial agent incorporated therein also acts as a barrier to organism infiltration. It contains antimicrobial agent that has dissolved from the cap 20 surfaces (such as one or more of the elongate member 33, male luer 31, and thread shield 48).

Figure 8A:
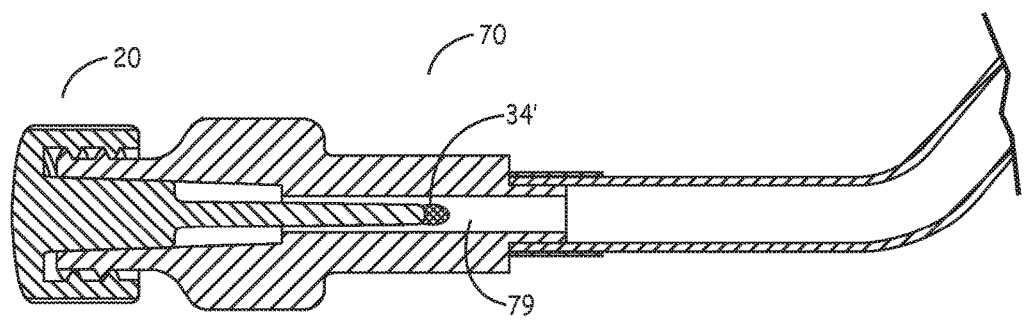
FIG. 8A is a side cross-section view of a cap with a swellable tip made in accordance with an implementation of the invention, inserted into a catheter. The tip is shown in its unswollen state.

FIG. 8A refers to an alternative embodiment of the cap 20 which possesses a novel tip 34' that has a diameter that is smaller than the diameter of the hub lumen 79 when the tip 34' is inserted into a catheter 70, but subsequently expands in size. This embodiment is especially beneficial when the cap 20 is used in a catheter 70 that does not have a clamp for confining the solution, or in cases where it is desirable to further limit the amount of antimicrobial agent required (less is required because the volume of confined solution is lower). The tip 34' is shown in FIG. 8A in its unswollen state during insertion in order to allow the elongate member to be easily inserted and to minimize its potential for pushing organisms distal to the tip 34' by a plowing action. The elongate member in a preferred embodiment remains sufficiently stiff while it is being inserted onto into the catheter 70 and it does not require any extra parts or aids for insertion.

Figure 8B:
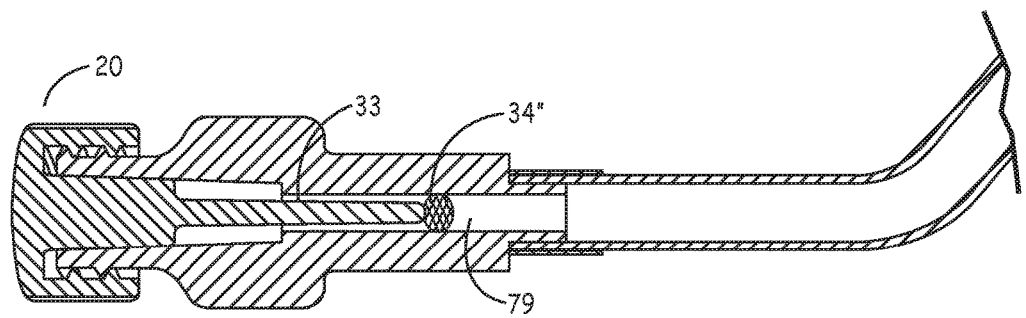
FIG. 8B is a side cross-section view of a cap with a swellable tip made in accordance with an implementation of the invention, inserted into a catheter. The tip is shown in its swollen state.

FIG. 8B refers to an alternative embodiment of the cap 20 as described in reference to FIG. 8A, except the tip 34" is shown in its swollen state. In the depicted embodiment the diameter of the tip 34" is equal to the diameter of the hub lumen 79 in its swollen state; the tip 34" preferably conforms to the surface of the hub lumen 79 as it swells. The swollen tip 34" is beneficial for confining the solution, or in cases where it is desirable to further limit the amount of antimicrobial agent required (less is required because the volume of confined solution is lower). The tip 34" is removable from the hub lumen 79 when reasonable removal force is applied to the cap 20. This is achieved by choosing the material and size the tip 34" such that, when it is in its swollen state, the normal force that the tip 34" applies to the wall of the hub lumen 79 is sufficiently low to allow acceptable removal force. In an example embodiment the diameter of the unswollen tip 34' (reference FIG. 8A) is 0.060 inches, the diameter of the confined swollen tip 34" is 0.098 inches (the same diameter as the hub lumen 79), and the diameter of the unconfined swollen tip is 0.110 inches when placed in normal saline. However, these diameters will vary to match the diameter of the device that the cap is being used with. The preferred unconfined swollen diameter (defined as the diameter the tip will expand to if it is not confined by a lumen wall) is slightly larger than the diameter of the hub lumen 79. An additional beneficial effect of the swollen tip is that it produces a scrubbing effect on the catheter wall that will physically remove organisms adhered to the interior wall section upon removing the cap from the catheter.

In one embodiment, the tip is manufactured to produce anisotropic swelling, such that the diameter increases but the length does not substantially increase. In another embodiment the entire elongate member is made of an anisotropically swelling material such that the diameter increases but the length does not substantially increase.

In one implementation, the material of the tip 34" consists of a swellable polyurethane, such as Lubrizol TG-500, that has been heat fused onto the elongate member 33 which is a non-swellable polyurethane, such as Lubrizol 1065D. These materials provide acceptable swelling, durability, strength and flexibility. The elongate member is coated with antimicrobial agent in an amount sufficient to obtain an adequate antimicrobial effect, yet low enough to remain safe for the patient.

Figure 9:
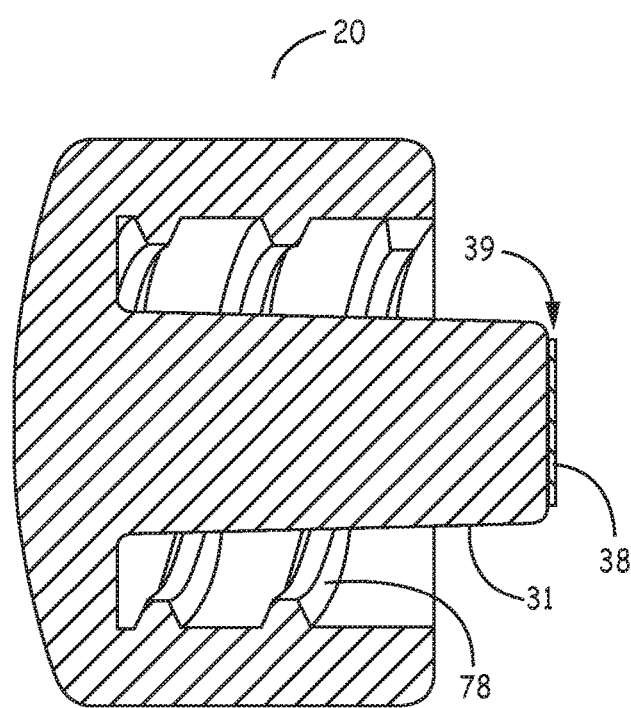
FIG. 9 is a side cross-section view of a cap not containing an elongate member made in accordance with an implementation of the invention.

In reference to FIG. 9, this alternative embodiment of the invention is useful in applications where an elongate member will not fit into a catheter because the internal diameter of the catheter is too small, such as with peripherally inserted central catheters (PICC). In this embodiment, the cap 20 does not contain an elongate member as in previous embodiments. Instead, the cap has a luer end face 38 that is flat or slightly recessed, and the end face 38 is coated with an antimicrobial layer 39. The preferred type and amount of antimicrobial in the antimicrobial layer 39 is the same as the elongate member (reference the description for FIG. 5C). Similarly, the male luer 31 and the catheter threads 78 preferably contain the same type and amount of antimicrobial agent as the other embodiments. The antimicrobial agent is preferably applied to the end face using a precision metering pump with 15% chlorhexidine acetate in a methanol solution. Other solvent, percentages and coating methods may be used.

Figure 10A:
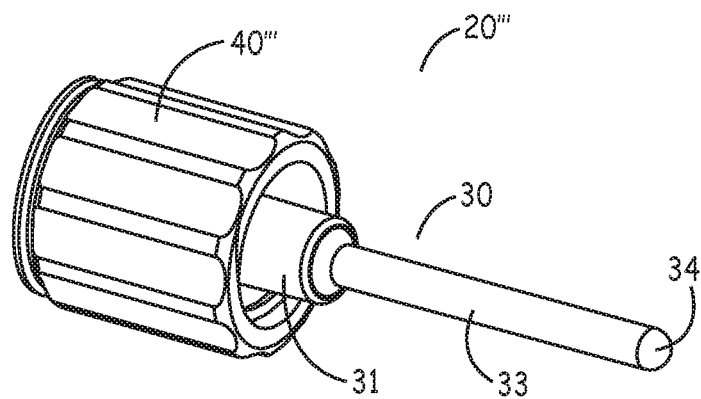
FIG. 10A is a perspective view, looking from the distal end of a cap, made in accordance with a preferred implementation of the invention.

In reference to FIG. 10A, an alternative embodiment of the invention is shown in which the cap 20''' is manufactured from two components, a retaining ring 40''' and an insert 30. It is desirable to have a highly controlled and repeatable amount of antimicrobial agent placed upon the desired regions of the cap 20'''. It is also preferred to have different amounts of antimicrobial on the different regions. It becomes easier to coat each region of the cap 20''' if the retaining ring 40''' is not blocking access to the male luer 31 (and vice versa). This is accomplished by manufacturing the cap 20''' as two separate pieces, the retaining ring 40''' and the insert 30. The preferred amount of antimicrobial agent within each region remains the same as presented above (refer to Ref. 5C).

Figure 10B:
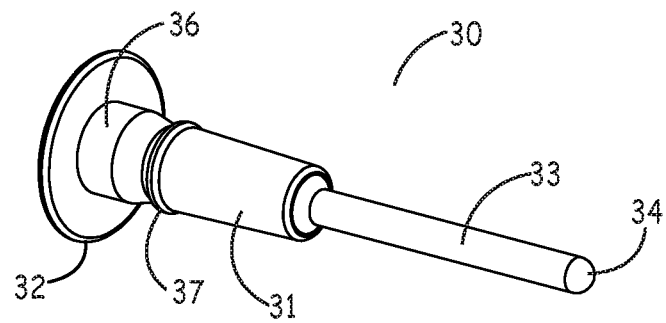
FIG. 10B is a perspective view, looking from the distal end of an insert, made in accordance with a preferred implementation of the invention.
Figure 10C:
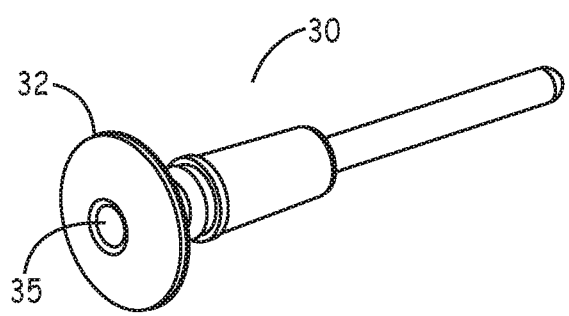
FIG. 10C is a perspective view, looking from the proximal end of an insert, made in accordance with a preferred implementation of the invention.

In reference to FIG. 10B, the insert 30 is coated with chlorhexidine acetate the elongate member 33 and along the male luer 31. The plate 32, cap shoulder 36, and the retaining flange 37 do not require coating. The two parts that are coated are the male luer 31 and the elongate member 33; contain the same amount of antimicrobial as referenced above In reference to FIG. 10C, the plate 32 at the proximal end of the insert 30 has a hole 35. The purpose of this hole 35 is to improve manufacturing. For instance, the hole 35 creates a convenient feature that can be used for holding and rotating the insert 30 to allow the part to be spun as it is being coated. The hole 35 also reduces shrinkage in the injected molded insert 30 by creating more uniform wall thickness.

Figure 10D:
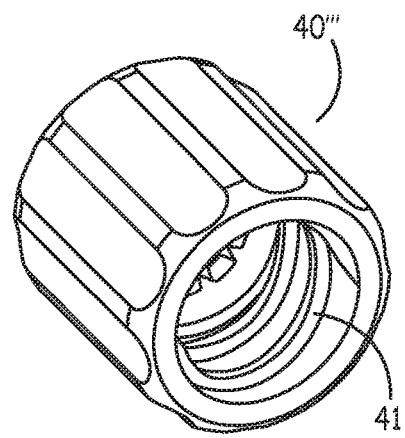
FIG. 10D is a perspective view, looking from the distal end of a retaining ring, made in accordance with a preferred implementation of the invention.

In reference to FIG. 10D, the retaining ring 40''' is a commercially available product from Value Plastics, Inc. with the exception that the cap threads 41 are coated with an antimicrobial agent. The antimicrobial agent in the preferred embodiment is chlorhexidine acetate in the same preferred amount as disclosed above. The retaining ring 40''' is readily coated using a spraying technique where the retaining ring 40''' is spun along its axis, and the antimicrobial is sprayed directly onto the cap threads. As an alternative coating method, the cap threads 41 were coated by filling the internal portion of the ring 40''' with 7% chlorhexidine methanol solution, subsequently draining the solution and allowing the parts to dry. This resulted in approximately 1.2 mg of chlorhexidine acetate on the cap threads 41. The dose of antimicrobial may be adjusted by adjusting the solution concentration.

Figure 10E:
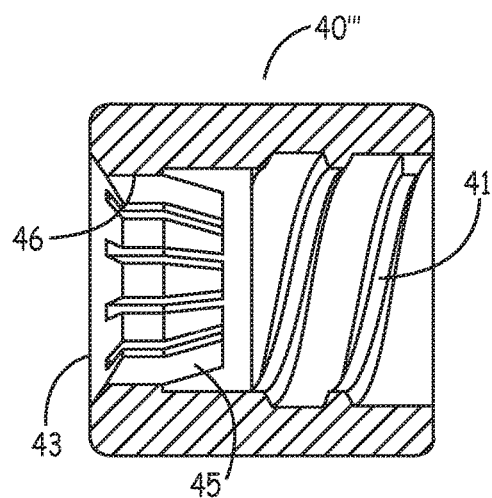
FIG. 10E is a side section view of a retaining ring made in accordance with a preferred implementation of the invention.

In reference to FIG. 10E, the retaining shoulder 46 comes into contact with the insert (not shown) when the insert is inserted inside the retaining ring 40'''. The proximal opening 43 is used to initially receive the insert 30 (refer to FIG. 10F) during assembly. The retaining fingers 45 are designed to retain the retaining ring 40''' onto the insert, as will be described in the reference below. The ring shoulder 46 helps secure the insert.

Figure 10F:
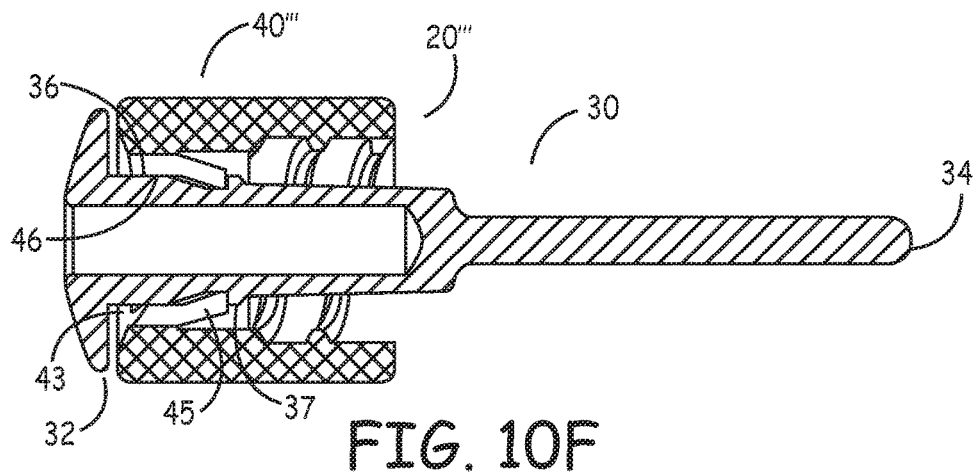
FIG. 10F is a side cross section view of a cap made in accordance with a preferred implementation of the invention.

In reference to FIG. 10F, the preferred embodiment for the two-piece cap 20''' is shown. The insert 30 is shown fully inserted into the retaining ring 40'''. The tip 34 was pushed through the proximal opening until retaining ring 40''' bottomed out on the plate 32. The retaining fingers 45 are engaged with the retaining flange 37 to secure the retaining ring 40''' on the insert 30.

It is desirable to have the retaining ring 40''' not rotate freely on the insert 30. Instead, it is preferred to have the torque be greater than 0 pound-inches (lb-in) but less than 2.0 lb-in. In a more preferred embodiment, the torque is between 0.1 lb-in and 1.25 lb-in. In the most preferred embodiment, the torque is between 0.2 lb-in and 0.5 lb-in. By controlling the diameter of the insert shoulder 36 such that it interferes with ring shoulder 46, the torque can be controlled as shown in the graph depicted in FIG. 11.

It is preferred to keep the interference between the ring shoulder 46 and the insert shoulder 36 within the range of 0.002 inch and 0.009 inch in order to keep the rotation torque within an acceptable range.

Antimicrobial Agent

An antimicrobial agent can be incorporated both into the elongate member material and/or on the elongate member surface of the present invention. In a preferred embodiment, the antimicrobial agent is chlorhexidine acetate; approximately 250 µg of chlorhexidine acetate is coated onto a 17 mm long×1.9 mm diameter rod-shaped elongate member, resulting in a chlorhexidine acetate layer approximately 2 µm thick along. The luer portion is coated with 50 µg of chlorhexidine acetate, resulting in a layer that is approximately 0.4 µm thick. It is also possible to inject an antimicrobial agent into the catheter using a syringe, or to deliver antimicrobial agents by way of the connector tip cavity (dry dissolvable amount, applicable for Citrate or others requiring large amounts of antimicrobial agent).

The elongate member has the added benefit of displacing fluid from within the catheter as it is inserted, transferring the solution to the outer proximal region of the catheter connector (end face and treads). Antimicrobial agent from the cap dissolves into the displaced fluid, and thereby disinfecting the proximal end of the connector. Furthermore, when the fluid dries, it deposits a coating of chlorhexidine acetate or other appropriate antimicrobial on the connector as described above. As an alternative to using the elongate member, is the chlorhexidine acetate or other antimicrobial agent may be delivered by a coating on a luer tip (such as 250 µg of chlorhexidine acetate in a layer that is approximately 20 µm thick).

An antimicrobial composition is located on the outer surface of the elongate member, the male luer connector, and the retaining ring The antimicrobial composition elutes from the elongate member after insertion of the elongate member/ rod into a catheter. When the system is inserted into the catheter, the antimicrobial agent dissolves into the fluid contained within the catheter, thus coming into contact with infectious organisms that might be present along the connector surfaces and lumen wall of the catheter or in solution. Additionally, the antimicrobial agent and any infectious organisms are confined together in the small space along within the catheter. Another benefit is that the confining action of the clamp traps any infectious microbes within the catheter and prevents them from being transmitted to other areas of the catheter or to the body to prevent a systemic infection.

The antimicrobial agents should kill and/or provide stasis of Gram-positive and Gram-negative bacteria and fungi. The agents may also have efficacy at killing organisms within an established biofilm and/or degrading the extracellular matrix of the film. However, this is not necessary for the invention to be beneficial because the invention is designed to kill organisms before they have an opportunity to form a biofilm. The preferred antimicrobial agent is chlorhexidine acetate, also known as chlorhexidine diacetate. Other compounds containing chlorhexidine may be used (such as chlorhexidine free base, chlorhexidine gluconate and chlorhexidine with dyes). Chlorhexidine acetate has an advantage over chlorhexidine gluconate because the risks associated with para chloroaniline may be minimized. Other suitable antimicrobial agents may also be used. In general, the preferred antimicrobials are soluble in water, they have a history of clinical use with a demonstrated safety profile, they are antibiotic-free, they can be applied onto a medical device, and they can be subsequently dissolved into a composition having an effective concentration to inhibit growth of bacterial and fungal organisms. Suitable materials include tetrasodium ethylenediaminetetraacetic acid (tetrasodium EDTA), sodium citrate (yielding a concentration of 30% or higher), iodine, taurolidine, disodium EDTA, silver compounds (including silver nanoparticles and ions), silver sulfadiazine, and, triclosan.

While one particular drug or antimicrobial agent may provide relief from a wide range of challenging organisms that could potentially lead to catheter-related bloodstream infection, two or more agents may be used to increase efficacy against a broad range of infectious organisms (bacteria and fungi).

In particular, catheter-related infections arise from three broad classes of organisms: fungi, Gram-negative bacteria, and Gram-positive bacteria. If an antimicrobial agent can be identified that would abate one or two of these types of organisms, while this would certainly be beneficial, it would leave the patient vulnerable to the remaining type(s). By pairing agents with different modes of action, infections by an increased spectrum of organisms can be prevented. This synergy would likely lead to further decreases in catheter-related morbidity and mortality, lessening the impact of the implanted catheter on the patient's quality of life. The preferred combinations of antimicrobial agents are chlorhexidine acetate and EDTA, silver sulfadiazine and sodium dodecyl sulfate, and silver sulfadiazine and methylene blue.

Although treating, preventing, and eliminating infectious organisms for the prevention of infections is the primary use of the cap, ancillary benefits can also be envisioned which would involve incorporating additional agents. An antithrombotic agent eluting from the elongate member can be used to improve the action of the heparin used currently in the locking solution. An enzyme or agent which promoted degradation of the extra-cellular matrix of biofilm (generally composed of polysaccharides) could enable use of the cap for treatment as well as prevention.

In principle, antibiotics (rifampin, minocycline, etc.) can be incorporated into the cap or similar device and be as effective as non-antibiotic antimicrobials. However, continuous exposure to one antibiotic can lead to antibiotic resistant bacteria strains, for example, methicillin resistant *S. aureus* (MRSA). Therefore, the preferred embodiment uses an antimicrobial agent selected from the subset of those which are not antibiotics. If, for some reason, an antibiotic is used, the risk of developing antibiotic resistant strains of bacteria may be mitigated by preparing a second, complimentary, cap containing a different antibiotic. By using the two caps in an alternating fashion with successive dialysis treatments, infectious organisms that are resistant to one antibiotic may be killed by the other.

Experiments have been conducted to examine the performance of the preferred embodiment of the invention, which is called "Pursuit Vascular's ClearGuard HD" or the "ClearGuard HD". These experiments demonstrate that the ClearGuard HD is effective at substantially reducing organisms within catheters as intended. Two of the experiments are highlighted below.

In an experiment conducted at Pursuit Vascular, coated caps were effective at consistently transferring more than 50 μg of chlorhexidine acetate (also referred to as chlorhexidine diacetate) onto the catheter's threads with a single connection. Such transfer provides the catheter with a means of further reducing infection-causing organisms which is replenished with every use of the invention. 10 μg or more of chlorhexidine is effective at reducing bacteria and other infection-causing organisms at the threads, and further preventing the organisms from infiltrating the catheter's connector end face, luer and lumen. Chlorhexidine acetate has a wide safety profile when used outside the catheter where there is little risk of it entering the bloodstream. A preferred range of chlorhexidine on the cap threads is 100 μg to 2500 μg. 500 μg to 1200 μg is more preferred.

For instance, if using a chlorhexidine based antimicrobial, approximately 50 μg of chlorhexidine acetate can be effective in some embodiments. This was demonstrated in an experiment conducted at Pursuit Vascular in which 50 μg of chlorhexidine was coated on the cap's luer portion. The caps containing the coated luers killed all of the *Candida albicans* that were seeded within the catheter's luer region. Within the same experiment, the *Candida albicans* remained viable when uncoated caps were used. Greater than 5 μg chlorhexidine acetate on the luer region is effective; 10 μg to 300 μg is preferred, and 30 μg to 80 μg is most preferred.

Laboratory testing conducted for Pursuit Vascular, Inc. demonstrated that 250 μg of chlorhexidine acetate on the elongate member produces greater than a 10,000× reduction in number of infection-causing organisms when the cap is used in a standard hemodialysis catheters containing saline, heparin-saline, or saline with 4% sodium citrate. The safety profile of the invention can be enhanced by limiting the amount of chlorhexidine acetate available to enter the bloodstream, the preferred maximum amount of chlorhexidine acetate on the elongate member is 2000 μg, more preferred is 1000 μg, and most preferred is 350 μg.

Experiment 1

The objective of this experiment was to assess the antimicrobial effectiveness of Pursuit Vascular's ClearGuard HD device in the most difficult clinically-relevant model. Since the ClearGuard HD is intended to be placed in catheter hubs, but not extend into the extension tubing, the catheter model was chosen to be a female luer connector, extension tube and clamp. The total length of the female luer connector and the extension tubing was manufactured to maximize the length and volume that would be expected to be encountered clinically. *Candida albicans* (fungus) was chosen as the challenge microorganism, because in previous tests *Candida albicans* was shown to be the most challenging microorganism for the ClearGuard HD to eradicate. *Candida albicans* were added to three different lock solutions: heparin-serum, saline-serum, and SDB broth. These solutions represent the most relevant (and challenging) solutions that would be expected clinically. The catheters were filled with the lock solutions and *Candida albicans*, next the caps (either the ClearGuard HD or a standard cap) were secured, and then the catheters were incubated for approximately 46 hours to simulate the time between dialysis sessions. After incubation, the caps were removed and the lock solution was tested for the presence of organisms.

Figure 11:
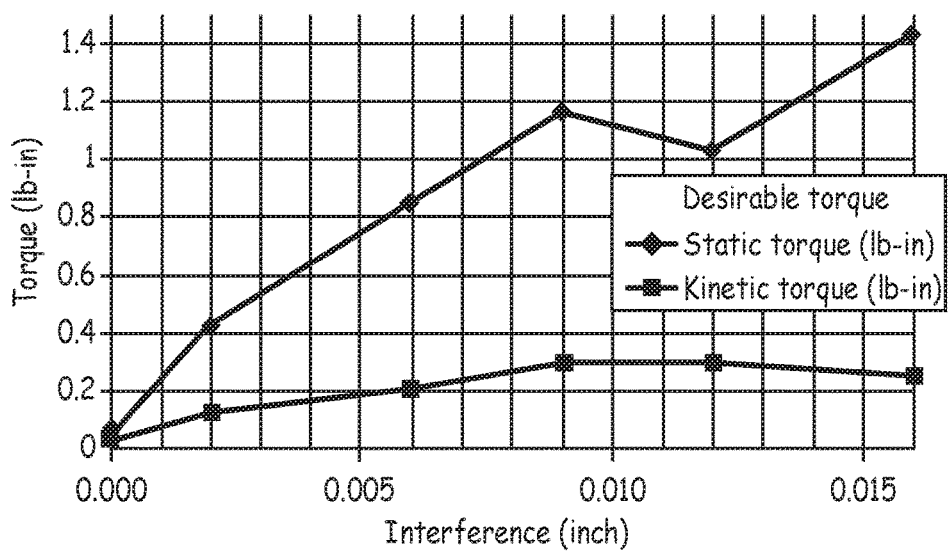
FIG. 11 is a table showing the effect of interference between a retaining ring and shoulder upon ring-insert torque.
Figure 12:
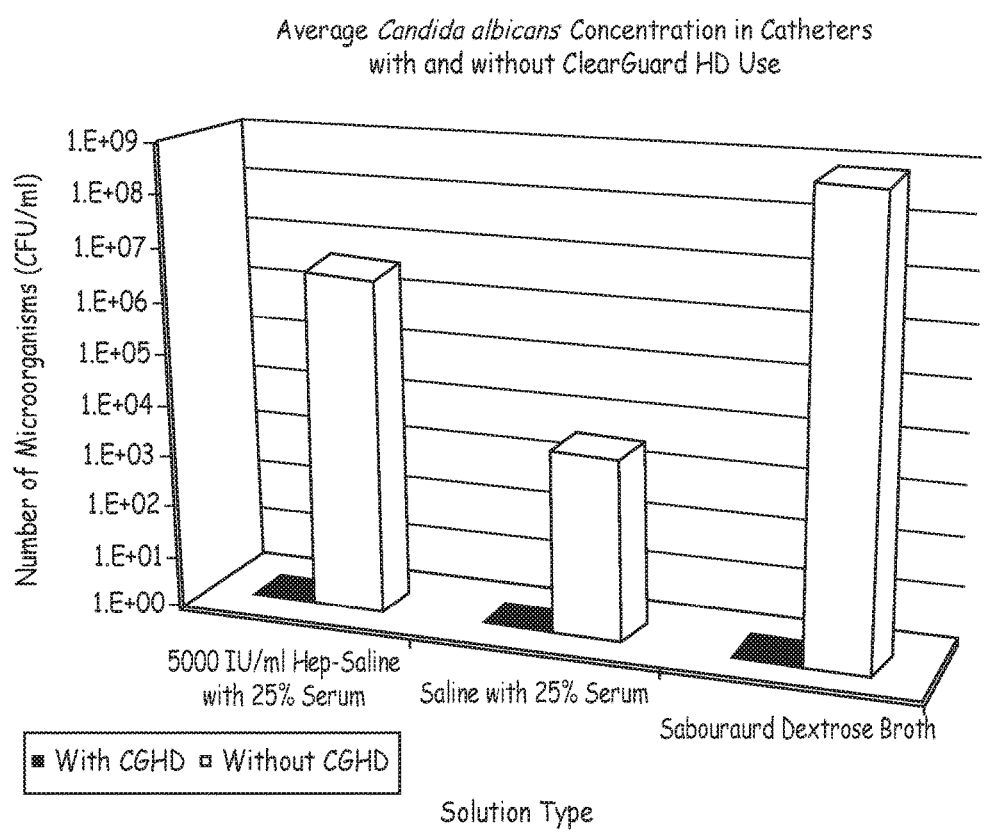
FIG. 12 shows concentration of microbes grown in various catheter conditions.

Experiment 1 results: The organism count is shown in FIG. 11 for ClearGuard HD caps and standard caps (shown as "with CGHD" and "without CGHD", respectively).

| Organism Count at Study End | | | |
| --- | --- | --- | --- |
| Solution | With CGHD | Without CGHD | Organism Reduction* |
| 5000 IU/ml Hep-Saline with 25% Serum | 0.0E+00 | 3.6E+06 | 3.6E+06 |
| Saline with 25% Serum | 0.0E+00 | 3.8E+03 | 3.8E+03 |
| SDB Broth | 0.0E+00 | 7.7E+08 | 7.7E+08 |

*Actual reduction in organism count is likely higher than calculated in this test because no organisms survived in the CGHD arm of the study.

The antimicrobial effectiveness of the ClearGuard HD was assessed against *Candida albicans*, the microorganism which has been the most difficult to eradicate when tested in a clinically relevant catheter model containing the most challenging and clinically relevant fluids.

All test samples using the ClearGuard HD had complete kill of the *Candida albicans*. In comparison, all control samples demonstrated growth of the CA. Since no *Candida albicans* survived during the ClearGuard HD portion of the test, the actual *Candida albicans* reduction may be significantly higher (better) than the sensitivity of this test. The minimum reduction of *Candida albicans*, when using the ClearGuard HD in place of a standard cap, was shown to be:
  a. $3.6 \times 10^6$ CFU/ml for Heparin with 25% Serum
  b. $3.8 \times 10^3$ CFU/ml for Saline with 25% Serum
  c. $7.7 \times 10^8$ CFU/ml for SDB Broth This test demonstrates that the ClearGuard HD produces a significant reduction in *Candida albicans* within a clinically relevant catheter and with clinically solutions. *Candida albicans* was previously shown to be the most difficult organism to reduce of the other clinically relevant microorganisms tested, therefore concluding that the ClearGuard HD produces broad-spectrum reduction in clinically relevant microorganisms.

Experiment 2

The objective of this experiment was to assess the relative rate of microorganism contamination in hemodialysis catheter lumens when using the ClearGuard HD versus standard caps in a simulated clinical environment. This experiment was intended to examine the effectiveness of the ClearGuard HD at preventing microorganism contamination of hemodialysis catheter lumens (both proximal and distal to the extension tubing clamp), compared to standard caps in a simulated clinical environment. Growth media was used inside of the catheter instead of the standard locking solution in order to provide an extremely sensitive means of detecting whether any microorganisms entered inside the catheter.

The primary route for infections-causing microorganisms to enter and colonize a hemodialysis (HD) catheter is generally accepted to be through the catheter's hub. During clinical use, hemodialysis catheter hubs are routinely exposed to microorganisms because the catheter and hub lies against the patient's skin. All commercially available catheter caps are primarily designed to keep fluid inside the catheter lumen but they are not well designed for preventing microorganisms from reaching and colonizing catheter lumens.

In order to compare whether the rate of microorganism colonization is affected by cap type (ClearGuard HD versus standard cap), twenty identical catheters were affixed to clothing, in a manner that would keep the catheters in contact with human skin, which occurs during clinical use. The catheters were kept in contact with the skin for a maximum of 26 days. Once a catheter's lumen was determined to be contaminated, the catheter was allowed to be removed from the study. The test consisted of two arms: 1) the ClearGuard HD arm, and 2) the standard cap arm. Except for the cap type used, the two arms were identical in all other ways (i.e., identical catheters, solutions, handling, etc.).

The study was designed to mimic the hemodialysis clinical practice as closely as practical. The entire volume of lock solution, including the solution distal to the clamp, was included in the microbiological testing to ensure with high probability that if any microorganisms were present anywhere within the catheter that they would be detected. Standard microbiological techniques were used to test for the presence of organisms.

Figure 13:
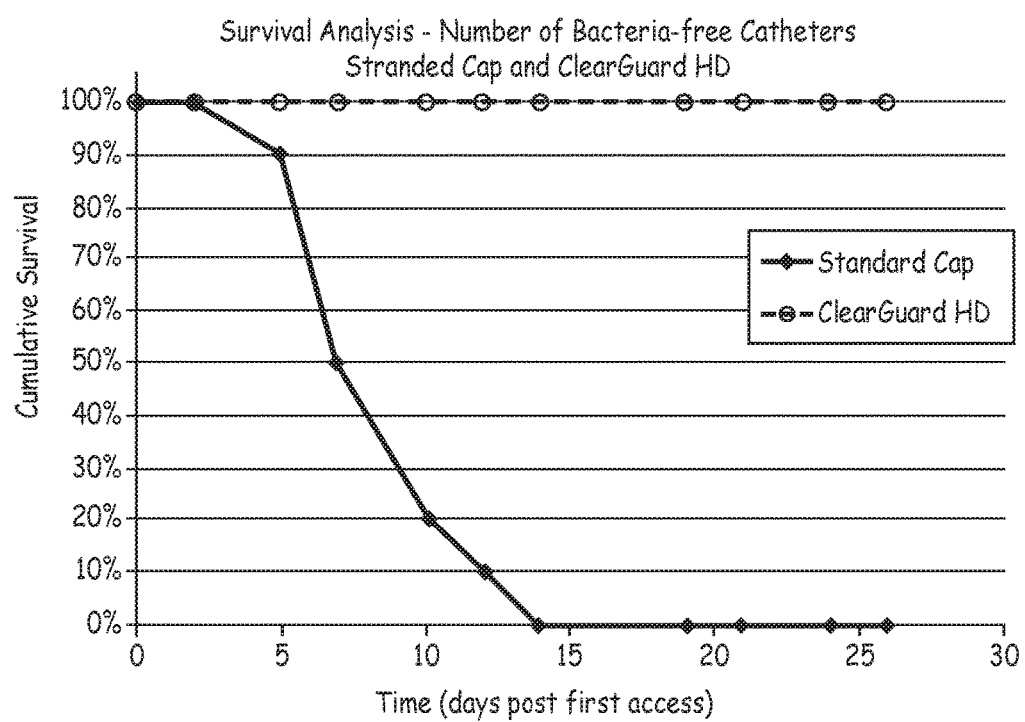
FIG. 13 shows a chart of survival analysis of bacteria-free catheters under various conditions.

The number of catheters that remained free from microorganism contamination as time progressed is illustrated in FIG. 13 below. Within fourteen days, all catheters using standard caps had become contaminated, while none of the catheters using the ClearGuard HD had become contaminated throughout the full twenty-six days of the experiment.

This experiment showed that, when catheters were filled with a growth media, were worn to simulate actual patient end use and were subjected to a standard dialysis fluid exchange schedule, the catheters using standard caps became contaminated with microorganisms at a mean time to failure of 8.9 days, and all of these catheters (10 out of 10) became contaminated by 14 days. In comparison, none of the catheters using the ClearGuard HD (0 out of 10) became contaminated throughout the entire 26 day test. The ClearGuard HD performs significantly better than standard caps (the current standard of care) at reducing microorganism contamination inside of catheters in a simulated clinical environment. While the invention has been particularly shown and described as referenced to the embodiments thereof, those skilled in the art will understand that the foregoing and other changes in form and detail may be made therein without departing from the spirit and scope of the invention.

What is claimed is:

1. A method of delivering antimicrobial to a catheter, the method comprising:
  filling at least a portion of the catheter with a liquid;
  using a clamp to block flow of the liquid from a proximal end to a distal end of the catheter; and
  inserting an elongate member into the proximal end of the catheter such that the elongate member is entirely proximal to the clamp so as to cause at least some of the liquid to flow out of a proximal opening of the catheter, wherein the elongate member includes the antimicrobial;
  wherein the elongate member is connected to a male luer connector, the male luer connector further comprises a tapered sealing member with a solid cross section.

2. The method of claim 1, further comprising delivering the antimicrobial to an exterior surface of the catheter.

3. The method of claim 2, wherein the exterior surface includes threads.

4. The method of claim 1, wherein at least some of the liquid that flows out of the proximal opening transfers to an exterior surface of the catheter.

5. The method of claim 4, wherein the liquid that transfers to the exterior surface of the catheter transfers the antimicrobial to the exterior surface of the catheter.

6. The method of claim 5, wherein the transferred antimicrobial forms a coating on the exterior surface of the catheter.

7. The method of claim 1, the male luer connector having an internal surface for engaging an exterior surface of the catheter, wherein the internal surface includes the antimicrobial.

8. The method of claim 1, wherein a coating on the elongate member includes the antimicrobial.

9. The method of claim 1, wherein blocking flow of the liquid into the distal end of the catheter includes closing the clamp onto the catheter proximal to the distal end to close a lumen of the catheter, prior to inserting the elongate member into the proximal end of the catheter.

10. The method of claim 9, further comprising delivering the antimicrobial from the elongate member into the catheter proximal to the clamp, wherein the clamp prevents the delivered antimicrobial from entering the catheter distal to the clamp.

11. The method of claim 1, further comprising dissolving the antimicrobial into the liquid within the portion of the catheter.

12. The method of claim 1, wherein the antimicrobial of the elongate member includes chlorhexidine.

13. A method of delivering an antimicrobial to a catheter containing a liquid, the method comprising:
　closing a clamp onto the catheter proximal to a distal end of the catheter to close a lumen of the catheter, thereby restricting flow of the liquid into the distal end of the catheter; and
　after closing the clamp, inserting an antimicrobial-containing elongate member into a proximal end of the catheter such that the antimicrobial-containing elongate member is entirely proximal to the clamp;
　wherein a male luer connector is connected to the antimicrobial-containing elongate member, the male luer connector further comprises a tapered sealing member with a solid cross section.

14. The method of claim 13, further comprising filling at least a portion of the catheter with the liquid, prior to closing the clamp.

15. The method of claim 14, wherein the liquid comprises heparin, saline, sodium citrate, or combinations thereof.

16. The method of claim 13, wherein inserting the antimicrobial-containing elongate member into the proximal end of the catheter causes at least some of the liquid to flow out of a proximal opening of the catheter.

17. The method of claim 16, the male luer connector having an internal surface for engaging an exterior surface of the catheter, wherein the internal surface includes antimicrobial, and wherein liquid that flows out of the proximal opening flows to the exterior surface of the catheter and transfers the antimicrobial of the internal surface to the exterior surface of the catheter.

18. The method of claim 17, wherein the internal surface of the male luer connector includes threads, and the exterior surface of the catheter includes threads.

19. The method of claim 13, wherein a coating on the antimicrobial-containing elongate member includes the antimicrobial.

20. The method of claim 19, further comprising dissolving the antimicrobial into the liquid within a portion of the catheter proximal to the clamp.

21. The method of claim 13, further comprising delivering the antimicrobial from the antimicrobial-containing elongate member into the catheter proximal to the clamp, wherein the clamp prevents the antimicrobial from entering the catheter distal to the clamp.

22. The method of claim 13, wherein the antimicrobial of the antimicrobial-containing elongate member includes chlorhexidine.

23. A method of delivering antimicrobial to a catheter, the method comprising:
　filling at least a portion of the catheter with a liquid;
　closing a clamp onto the catheter proximal to a distal end of the catheter to close a lumen of the catheter, thereby restricting flow of the liquid into the distal end of the catheter;
　after closing the clamp, inserting an elongate member into a proximal end of the catheter to cause the liquid to flow out of a proximal opening of the catheter, wherein the elongate member includes antimicrobial, wherein the antimicrobial of the elongate member transfers from the elongate member into the catheter proximal to the clamp, and the clamp prevents the transferred antimicrobial from entering the catheter distal to the clamp; and
　engaging an exterior surface of the catheter with an internal surface of a male luer connector, the male luer connector being connected to the elongate member, wherein the internal surface of the male luer connector includes antimicrobial, wherein the liquid that flows out of the proximal opening flows to the exterior surface of the catheter and transfers the antimicrobial of the internal surface to the exterior surface of the catheter, and wherein the elongate member is entirely proximal to the clamp during the inserting and engaging steps;
　wherein the male luer connector includes a tapered member with a solid cross section.

24. The method of claim 23, further comprising dissolving the first antimicrobial transferred from the elongate member into the liquid within the catheter proximal to the clamp.

25. The method of claim 23, wherein the antimicrobial of the elongate member or the antimicrobial of the internal surface includes chlorhexidine.

26. The method of claim 23, wherein the clamp is closed after the filling step.

27. The method of claim 23, wherein the exterior surface of the catheter includes threads that mate with threads of the internal surface of the male luer connector.

28. The method of claim 23, wherein the antimicrobial that is transferred to the exterior surface of the catheter forms a coating on the exterior surface of the catheter.

\* \* \* \* \*